United States Patent
Liu et al.

(10) Patent No.: US 11,708,391 B2
(45) Date of Patent: *Jul. 25, 2023

(54) RAPAGLUTINS, NOVEL INHIBITORS OF GLUT AND USE THEREOF

(71) Applicant: The Johns Hopkins University, Baltimore, MD (US)

(72) Inventors: Jun Liu, Baltimore, MD (US); Jingxin Wang, Baltimore, MD (US); Zufeng Guo, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 915 days.

This patent is subject to a terminal disclaimer.

(21) Appl. No.: 16/074,300

(22) PCT Filed: Feb. 3, 2017

(86) PCT No.: PCT/US2017/016516
§ 371 (c)(1),
(2) Date: Jul. 31, 2018

(87) PCT Pub. No.: WO2017/136731
PCT Pub. Date: Aug. 10, 2017

(65) Prior Publication Data
US 2021/0214390 A1    Jul. 15, 2021

Related U.S. Application Data

(60) Provisional application No. 62/291,453, filed on Feb. 4, 2016.

(51) Int. Cl.
  *C07K 5/10*        (2006.01)
  *C07K 5/103*       (2006.01)
  (Continued)

(52) U.S. Cl.
  CPC .......... *C07K 5/1008* (2013.01); *A61K 9/0019* (2013.01); *A61K 31/12* (2013.01);
  (Continued)

(58) Field of Classification Search
None
See application file for complete search history.

(56) References Cited

U.S. PATENT DOCUMENTS

| 5,212,155 A | 5/1993 | Calne |
| 5,457,194 A | 10/1995 | Luly et al. |

(Continued)

FOREIGN PATENT DOCUMENTS

| JP | 8-333256 H | 12/1996 |
| JP | 2011-524413 | 9/2011 |

(Continued)

OTHER PUBLICATIONS

Panchenko et al. ('Prediction of functional sites by analysis of sequence and structure conservation' Protein Science 2004 v13 pp. 884-892) (Year: 2004).*

(Continued)

*Primary Examiner* — Ronald T Niebauer
(74) *Attorney, Agent, or Firm* — DLA Piper LLP (US)

(57) ABSTRACT

Compounds with the following structures

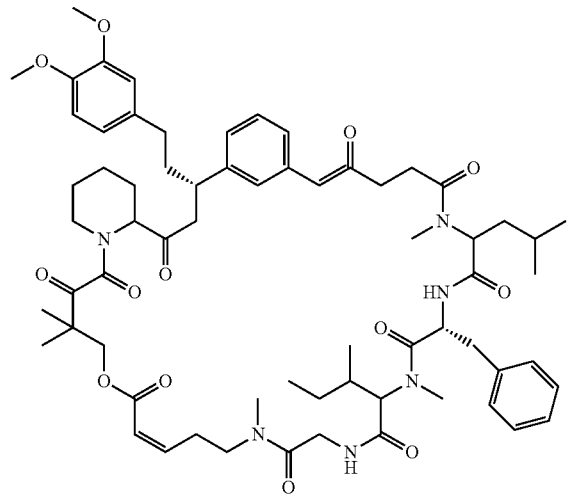

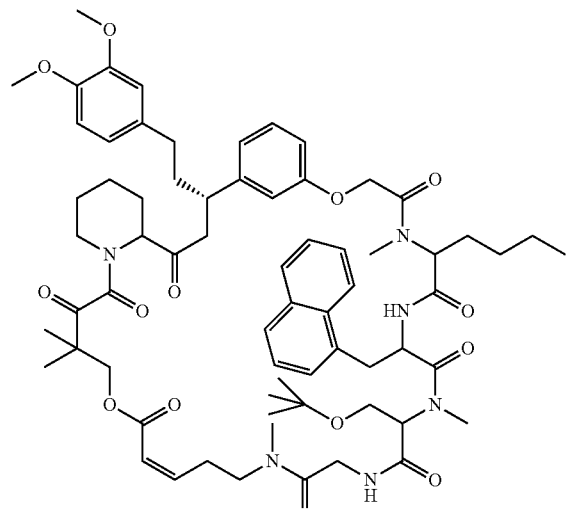

and their analogs are provided. Compositions that include these structures can be used to inhibit glucose transporters and stop or decrease the proliferation of cancer, treat possible organ rejection and treat autoimmune disease.

4 Claims, 19 Drawing Sheets

(51) Int. Cl.

| | | |
|---|---|---|
| *A61P 35/00* | (2006.01) | |
| *A61K 9/00* | (2006.01) | |
| *A61K 31/12* | (2006.01) | |
| *A61K 31/167* | (2006.01) | |
| *A61K 31/235* | (2006.01) | |
| *A61K 31/353* | (2006.01) | |
| *A61K 31/407* | (2006.01) | |
| *A61K 31/4406* | (2006.01) | |
| *A61K 38/12* | (2006.01) | |
| *A61K 45/06* | (2006.01) | |
| *C07K 5/117* | (2006.01) | |
| *C07K 5/12* | (2006.01) | |

(52) U.S. Cl.
CPC .......... *A61K 31/167* (2013.01); *A61K 31/235* (2013.01); *A61K 31/353* (2013.01); *A61K 31/407* (2013.01); *A61K 31/4406* (2013.01); *A61K 38/12* (2013.01); *A61K 45/06* (2013.01); *A61P 35/00* (2018.01); *C07K 5/1024* (2013.01); *C07K 5/12* (2013.01); *C07K 5/126* (2013.01)

(56) References Cited

U.S. PATENT DOCUMENTS

| | | | |
|---|---|---|---|
| 5,527,907 | A | 6/1996 | Or et al. |
| 5,798,355 | A | 8/1998 | Steiner et al. |
| 6,984,635 | B1 | 1/2006 | Schreiber et al. |
| 7,056,935 | B2 | 6/2006 | Steiner et al. |
| 7,358,235 | B2 | 4/2008 | Puetz et al. |
| 7,803,808 | B2 | 9/2010 | Gregory et al. |
| 7,989,395 | B2 | 8/2011 | Morgan et al. |
| 8,642,215 | B2 | 2/2014 | Kim et al. |
| 8,956,825 | B2 | 2/2015 | Weisbart |
| 9,250,237 | B2 | 2/2016 | Liu et al. |
| 9,840,518 | B2 | 12/2017 | Hird et al. |
| 9,989,535 | B2 | 6/2018 | Verdine et al. |
| 10,466,249 | B2 | 11/2019 | Verdine et al. |
| 10,533,016 | B2 | 1/2020 | Verdine et al. |
| 10,662,220 | B2 * | 5/2020 | Liu ................. C07K 1/047 |
| 10,774,110 | B2 * | 9/2020 | Liu ................. A61P 1/16 |
| 2002/0052410 | A1 | 5/2002 | Steiner et al. |
| 2006/0003362 | A1 | 1/2006 | Zerangue |
| 2008/0292618 | A1 | 11/2008 | Weisbart |
| 2008/0306098 | A1 | 12/2008 | Mutz et al. |
| 2009/0253732 | A1 | 10/2009 | Gregory et al. |
| 2014/0073581 | A1 | 3/2014 | Liu et al. |
| 2014/0206624 | A1 | 7/2014 | Sykes et al. |
| 2015/0018340 | A1 | 1/2015 | Gopalakrishnan et al. |
| 2015/0050356 | A1 | 2/2015 | Desai et al. |
| 2015/0203512 | A1 | 7/2015 | Reger et al. |
| 2017/0305926 | A1 | 10/2017 | Hird et al. |
| 2019/0224274 | A1 | 7/2019 | Dawson et al. |
| 2020/0040004 | A1 | 2/2020 | Liu et al. |

FOREIGN PATENT DOCUMENTS

| | | |
|---|---|---|
| JP | 6891183 B2 | 6/2021 |
| WO | WO 1996/40140 | 12/1996 |
| WO | WO 2004/093798 | 11/2004 |
| WO | WO 2010/004304 | 1/2010 |
| WO | WO 2012/075048 | 6/2012 |
| WO | WO 2014/201405 | 12/2014 |
| WO | WO 2018/045250 | 3/2017 |
| WO | WO 2017/136708 | 8/2017 |
| WO | WO 2017/136717 | 8/2017 |
| WO | WO 2017/136731 | 8/2017 |
| WO | WO 2019/064182 | 4/2019 |

OTHER PUBLICATIONS

Amigo: A Novel Tag Analysis Methodology That Enables Detection of Molecules from DNAEncoded Chemical Libraries. SLAS Discovery 2018,23(5), 397-404. 10.1177/2472555217753840.

Arico-Muendel, From haystack to needle: finding value with DNA encoded library technology at GSK MedChemComm, (2016) 7(10): 1898-1909.

Bao, Krylov Predicting Electrophoretic Mobility of Protein-Ligand Complexes for Ligands from DNA-Encoded Libraries of Small Molecules Anal. Chem., (2016) 88 (10):5498-5506.

Bauerle et al., "Adenosine Generation and Signaling during Acute Kidney Injury", J Am Soc Nephrol, 2011, 22:14-20.

Blaksjaer, Fidelity by design: Yoctoreactor and binder trap enrichment for smallmolecule DNA-encoded libraries and drug discovery. Curr Opin Chem Biol. 2015;26:62-71. doi:10.1016/j.cbpa.2015.02.003.

Brown et al., Retrospective on Cholesterol Homeostasis: The Central Role of Scap. Annu Rev Biochem. 2018;87:783-807. doi:10.1146/annurev-biochem-062917-011852.

Buller et al. Design and synthesis of a novel DNAencoded chemical library using Diels-Alder cycloadditions. Bioorg Med Chem Lett. 2008;18(22):5926-5931. doi:10.1016/j.bmcl.2008.07.038.

Buller et al. Drug Discovery with DNA-Encoded Chemical Libraries Bioconjugate Chem. (2010) 21, 1571-80.

Buller, High-throughput sequencing for the identification of binding molecules from DNA-encoded chemical libraries Bioorg Med Chem Lett. (2010) 15;20(14):4188-92.

Castanon, Design and Development of a Technology Platform for DNA-Encoded Library Production and Affinity Selection [published correction appears in SLAS Discov. Jun. 2018;23 (5):489]. SLAS Discov. 2018;23(5):387-396. doi:10.1177/2472555217752091.

Chakraborty et al: "Design and synthesis of a rapamycin-based high affinity binding FKPB12 ligand"; Chemistry & Biology, Mar. 1995, 2, 157-161.

Chan et al,. Novel selection methods for DNA-encoded chemical libraries. Curr Opin Chem Biol. 2015;26:55-61. doi:10.1016/j.cbpa.2015.02.010.

Chen et al., "Adenosine receptors as drug targets—what are the challenges?", Nat Rev Drug Discov., Apr. 2013, 12(4):265-286.

Choi et al. "Structure of the FKBP12-Rapamycin Complex Interacting with the Binding Domain of Human FRAP" Science 273:239-242 (1996).

Choi et al., "The type 1 equilibrative nucleoside transporter regulates ethanol intoxication and preference", Nature Neuroscience, Aug. 2004, 7(8):855-861.

Clark et al. Design, synthesis and selection of DNA-encoded small-molecule libraries [published correction appears in Nat Chem Biol. Oct. 2009;5(10):772]. Nat Chem Biol. 2009;5(9):647-654. doi:10.1038/nchembio.211.

Clark, Selecting chemicals: the emerging utility of DNA-encoded libraries Curr Opin Chem Biol. (2010) 14(3):396-403.

Connors et al. DNA-encoded chemical libraries of macrocycles. Curr Opin Chem Biol. 2015;26:42-47. doi:10.1016/j.cbpa.2015.02.004.

Cuozzo et al. Discovery of a Potent BTK Inhibitor with a Novel Binding Mode by Using Parallel Selections with a DNA-Encoded Chemical Library BioChem (2017), 18(9):864-71.

Decurtins et al. Automated screening for small organic ligands using DNA-encoded chemical libraries. Nat Protoc. 2016;11(4):764-780. doi:10.1038/nprot.2016.039.

Deng et al. Discovery, SAR, and X-ray Binding Mode Study of BCATm Inhibitors from a Novel DNA-Encoded Library Bioconjug Chem. (2017) 20;28(9):2293-2301.

Denton, Crosslinking of DNA-linked ligands to target proteins for enrichment from DNA-encoded libraries. Medchemcomm. 2016;7(10):2020-2027. doi:10.1039/C6MD00288A.

Ding et al. Discovery of Potent and Selective Inhibitors for ADAMTS-4 through DNA-Encoded Library Technology (ELT). ACS Med Chem Lett. 2015;6(8):888-893. Published Jul. 7, 2015. doi:10.1021/acsmedchemlett.5b00138.

Ding, Design and Synthesis of Biaryl DNA-Encoded Libraries ACS Comb Sci. (2016) 10;18(10):625-629.

Eidam et al, Analysis of the productivity of DNA encoded libraries MedChemComm, (2016) 7(7): 1323-1331.

(56) References Cited

OTHER PUBLICATIONS

Estevez, A carbohydrate-derived trifunctional scaffold for DNA-encoded Libraries Tetrahedron: Asymmetry. (2017) 28:837-842.
European Search Report and Search Opinion Received for EP Application No. 17748264.3, dated Aug. 16, 2019, 18 pages.
Extended European Search Report dated Jul. 16, 2019, regarding EP 17 74 8270.
Franzini et al. Identification of structure-activity relationships from screening a structurally compact DNA-encoded chemical library. Angew Chem Int Ed Engl. 2015;54(13):3927-3931. doi:10.1002/anie.201410736.
Franzini et al. Interrogating target-specificity by parallel screening of a DNA-encoded chemical library against closely related proteins Chem Commun. (2015) 11;51(38):8014-16.
Franzini et al., DNA-Encoded Chemical Libraries: Advancing beyond Conventional Small-Molecule Libraries Acc Chem Res. (2014) 15;47(4):1247-55.
Franzini et al., Evaluation and Optimization of Modification Reactions of Oligonucleotides with Amines and Carboxylic Acids for the Synthesis of DNA-Encoded Chemical Libraries Bioconjug Chem. (2014) 20;25(8):1453-61.
Gartner et al., DNA-templated organic synthesis and selection of a library of macrocycles. Science. 2004;305(5690):1601-1605. doi:10.1126/science.1102629.
Grenz et al., "Equilibrative nucleoside transporter 1 (ENT1) regulates postischemic blood flow during acute kidney injury in mice", J Clin Invest., 2014, 124(6):2807-2807.
Grenz et al., "The Reno-Vascular A2B Adenosine Receptor Protects the Kidney from Ischemia", PLoS Medicine, Jun. 2008, 5(6):968-986.
Griffith et al., "Nucleoside and nucleobase transport systems of mammalian cells", Biochimica et Biophysica Acta, 1996, 1286:153-181.
Guo et al. Rapamycin-inspired macrocycles with new target specificity. Nat Chem. 2019;11(3):254-263. doi:10.1038/s41557-018-0187-4.
Halford, Breakthroughs with Bar Codes C&EN, (2017) 95(25): 28-33.
Harris et al. DNA-Encoded Library Screening Identifies Benzo[b][1,4]oxazepin-4-ones as Highly Potent and Monoselective Receptor Interacting Protein 1 Kinase Inhibitors. J Med Chem. 2016; 59(5):2163-2178. doi:10.1021/acs.jmedchem.5b01898.
Hong, "Rapamycin-based macrocyclic library development and Equilibrative Nucleoside Transporter 1 (ENT1) inhibition", A dissertation submitted to John Hopkins University in conformity with the requirements for the degree of Doctor of Philosophy, Jun. 2016, 134 pages.
Huang et al.: "Inhibition of Nucleoside Transport by Protein Kinase Inhibitors"; J. Pharmacology and Experimental Therapeutics, vol. 304, No. 2, Jan. 1, 2003, pp. 753-760, XP008036291, ISSN: 0022-3565, DOI: 10.1124/JPET.102.044214.
JP Office Action in Japanese Application No. 2018-540114, dated Jan. 26, 2021, 8 pages (with English translation).
JP Office Action in Japanese Application No. 2018-540115, dated Jan. 12, 2021, 8 pages (with English translation).
JP Office Action dated Oct. 27, 2020, regarding JP 2018-540102.
Keefe et al., Chemical ligation methods for the tagging of DNA-encoded chemical libraries. Curr Opin Chem Biol. 2015;26:80-88. doi:10.1016/j.cbpa.2015.02.015.
Kleiner et al., Small-molecule discovery from DNA-encoded chemical libraries Chem Soc Rev. (2011) 40(12): 5707-17.
Krall et al., Small targeted cytotoxics: current state and promises from DNA-encoded chemical libraries. Angew Chem Int Ed Engl. 2013;52(5):1384-1402. doi:10.1002/anie.201204631.
Kuai et al., Randomness in DNA encoded library selection data can be modeled for more reliable enrichment calculation. SLAS Discov. 2018;23(5):405-416.
Li et al. Quantitative PCR is a Valuable Tool to Monitor the Performance of DNA-Encoded Chemical Library Selections. Chembiochem. 2017;18(9):848-852. doi:10.1002/cbic.201600626.
Li et al., "Inhibition of human equilibrative nucleoside transporters by dihydropyridine-type calcium channel antagonists", European Journal of Pharmacology, 2007, 568:75-82.
Lim, Making ring compounds for DNA encoded libraries C&EN, (2017) 95 (29):10.
Lin et al., "Synthesis, Flow Cytometric Evaluation, and Identification of Highly Potent Dipyridamole Analogues as Equilibrative Nucleoside Transporter 1 Inhibitors", J. Med. Chem., 2007, 50:3906-3920.
Machutta et al. Prioritizing multiple therapeutic targets in parallel using automated DNA—encoded library screening. Nat Commun 8, 16081(2017). https://doi.org/10.1038/ncomms16081.
Mannocci et al. High-throughput sequencing allows the identification of binding molecules isolated from DNA-encoded chemical libraries. Proc Natl Acad Sci U S A. 2008; 105(46):17670-17675. doi:10.1073/pnas.0805130105.
Mannocci et al., 20 years of DNA-encoded chemical libraries Chem. Commun. (2011) 47:12747-53.
Mannocci et al., Isolation of Potent and Specific Trypsin Inhibitors from a DNA-Encoded Chemical Library Bioconjugate Chem. (2010) 21, 1836-41.
Melendez et al., "Last call for adenosine transporters", Nature Neuroscience, Aug. 2004, 7(8): 795-796.
Melkko et al. Encoded self-assembling chemical libraries. Nat Biotechnol. 2004;22(5):568-574 doi:10.1038/nbt961.
Mohamadnejad et al., "Adenosine Inhibits Chemotaxis and Induces Hepatocyte-Specific Genes in Bone Marrow Mesenchymal Stem Cells", Hepatology, Mar. 2010, 51(3):963-973.
Nakanishi "Drug Transporters as Targets for Cancer Chemotherapy," Cancer Genomics & Proteomics (2007), 4:241-254.
Neri Lerner RA. DNA-Encoded Chemical Libraries: A Selection System Based on Endowing Organic Compounds with Amplifiable Information. Annu Rev Biochem. 2018;87:479-502. doi:10.1146/annurev-biochem-062917-012550.
Neri, Twenty-five Years of DNA-Encoded Chemical Libraries Chembiochem. (2017) 4;18(9):827-828.
Passer et al., "Identification of then ENT1 antagonists dipyridamole and dilazep as amplifiers of oncolytic herpes simplex virus-1 replication", Cancer Res., May 2010, 70(10):3890-3895.
PCT International Preliminary Report on Patentability received for PCT Patent Application No. PCT/US17/16481, dated Aug. 16, 2018, 7 pages.
PCT International Search Report and Written Opinion in International Application No. PCT/US2020/53486, dated Jan. 8, 20201, 8 pages.
PCT International Search Report and Written Opinion in International Application No. PCT/US2020/53549, dated Feb. 4, 2021, 9 pages.
PCT International Search Report and Written Opinion received for PCT Patent Application No. PCT/US17/16481, dated Apr. 21, 2017, 7 pages.
Pennycooke et al., "Differential Expression of Human Nucleoside Transporters in Normal and Tumor Tissue", Biochemical and Biophysical Research Communications, 2001, 280:951-959.
Sachdeva et al., "Adenosine and its receptors as therapeutic targets: An overview", Saudi Pharmaceutical Journal, 2013, 21:245-253.
Salamon, Chemical Biology Probes from Advanced DNA-encoded Libraries ACS Chem Biol. (2016) 19;11 (2):296-307.
Satz et al. Analysis of Current DNA Encoded Library Screening Data Indicates Higher False Negative Rates for Numerically Larger Libraries ACS Comb Sci. (2017) 10;19(4):234-238.
Satz, DNA Compatible Multistep Synthesis and Applications to DNA Encoded Libraries Bioconjug Chem. (2015) 19;26(8):1623-32.
Satz, DNA Encoded Library Selections and Insights Provided by Computational Simulations ACS Chem Biol. (2016) 16;10(10):2237-45.
Satz, Simulated Screens of DNA Encoded Libraries: The Potential Influence of Chemical Synthesis Fidelity on Interpretation of Structure-Activity Relationships CS Comb. Sci. (2016) 18 (7):415-424.
Scheuermann et al., DNA-Encoded Chemical Libraries for the Discovery of MMP-3 Inhibitors Bioconjugate Chem. 2008, 19, 778-785.

(56) References Cited

OTHER PUBLICATIONS

Scheuermann et al., Dual-pharmacophore DNA-encoded chemical libraries Curr Opin Chem Biol. (2015) 26:99-103.

Shi et al. Recent advances on the encoding and selection methods of DNA-encoded chemical library. Bioorg Med Chem Lett. 2017;27(3):361-369. doi:10.1016/j.bmcl.2016.12.025.

Shi et al., "Selecting a DNA-Encoded Chemical Library against Non-immobilized Proteins Using a "Ligate-Cross-Link-Purify" Strategy", Bioconjugate Chemistry, 2017, 28:2293-2301.

Skopic, Acid- and Au(I)-mediated synthesis of hexathymidine-DNA-heterocycle chimeras, an efficient entry to DNA-encoded libraries inspired by drug structures Chem Sci. (2017) 1;8(5):3356-3361.

Skopic, Design and synthesis of DNA-encoded libraries based on a benzodiazepine and a pyrazolopyrimidine scaffold MedChemComm, (2016) 7(10): 1957-1965.

Tromp et al., "Inhibition of Nucleoside Transport by New Analogues of 4-Nitrobenzylthiosine: Replacement if the Ribose Moiety by Substituted Benzyl Groups", J. Med. Chem., 2004, 47:5441-5450.

Upadhyaya et al.: "Inhibition of Ras Signaling by Blocking Ras-Effector Interactions with Cyclic Peptides"; Angewandte Chemie International, 2015, 54, 7602-7606.

Visser et al., "Residues 334 and 338 in Transmembrane Segment 8 of Human Equilibrative nucleoside Transporter 1 Are Important Determinants of Inhibitor Sensitivity, Protein Folding, and Catalytic Turnover", Journal of Biological Chemistry, May 2007, 282(19):14148-14157.

Wen et al "Adenosine Signaling Good or Bad in Erectile Function?" Arterioscler Thromb Vasc Biol, Apr. 2012, 32:845-850.

Wrenn et al., Chemical Evolution as a Tool for Molecular Discovery Annu. Rev. Biochem. (2007) 76:331-49.

Wu et al.: "Creating diverse Target Binding Surfaces on FKBP12: Synthesis and Eavaluation of a Rapamycin Analogue Library"; ACS Combinatorial Science, 2011, 13, 486-495.

Wu et al.: "Inhibition of Ras-Effector Interaction by Cyclic Peptides"; Medchemcomm, Feb. 1, 2013, 4(2), 378-382.

Xia et al., Development and design of the tertiary amino effect reaction for DNA-encoded library synthesis. MedChemComm 2016;7(7),1316-1322.

Xu et al., "ENT1 Inhibition Attenuates Epileptic Seizure Severity Via Regulation of Glutamatergic Neurotransmission", Neuromol Med, 2015, 17:1-11.

Yuen et al., Achievements, Challenges, and Opportunities in DNA Encoded Library Research: An Academic Point of View Chembiochem. (2017) 4;18(9):829-836.

Zhang, "Protein Tyrosine Phosphatases: Structure and Function, Substrate Specificity, and Inhibitor Development", Annu. Rev. Pharmacol. Toxicol., 42:209-234, 2002.

Zimmerman et al., DNA-encoded chemical libraries: foundations and applications in lead discovery Drug Discov. Today (2016) 21(11):1828-1834.

Zimmerman et al. Hit-Validation Methodologies for Ligands Isolated from DNA-Encoded Chemical Libraries. Chembiochem. 2017;18(9):853-857. doi:10.1002/cbic.201600637.

Zimmerman et al., "Equilibrative nucleoside transporter (ENT)-1-dependent elevation of extracellular adenosine protects the liver during ischemia and reperfusion", Hepatology, Nov. 2013, 58(5):1766-1778.

JP Office Action in Japanese Application No. JP-A-2021-088242, dated Apr. 5, 2022, 6 pages (with English translation).

* cited by examiner

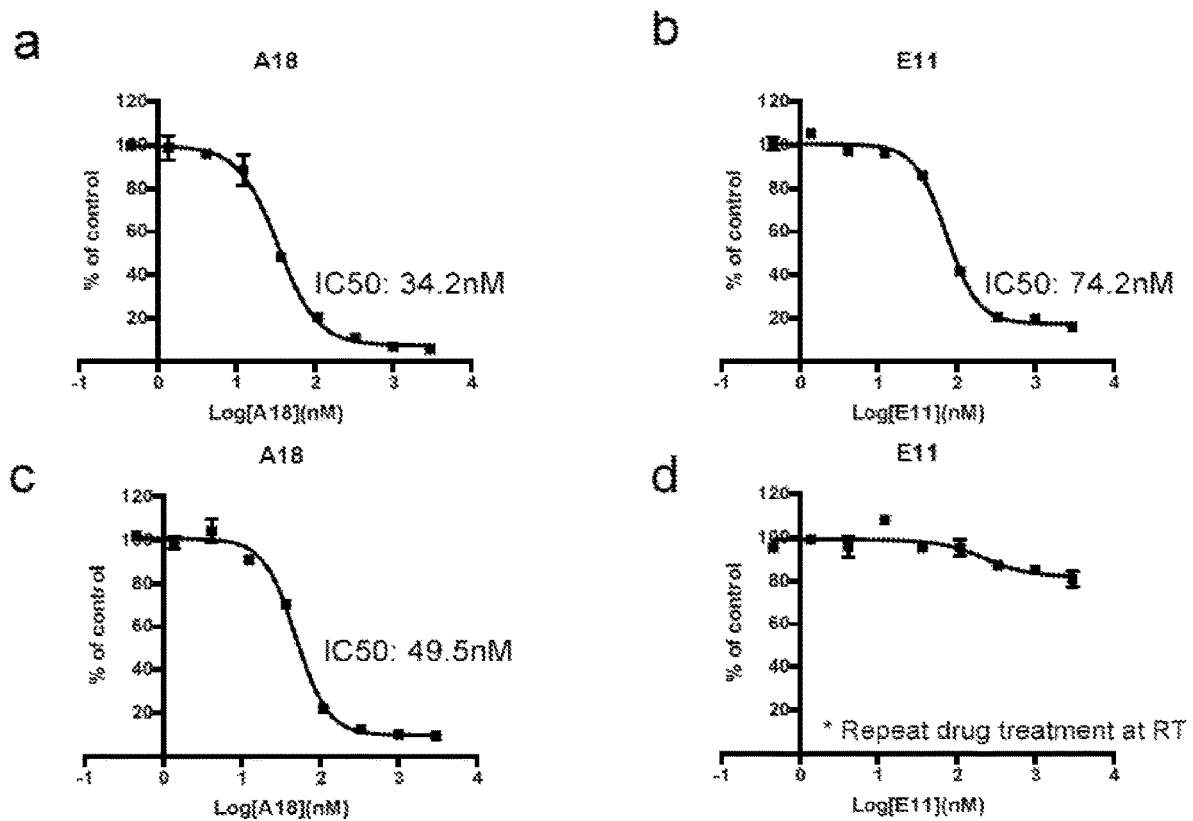
FIGURES 3A-3D
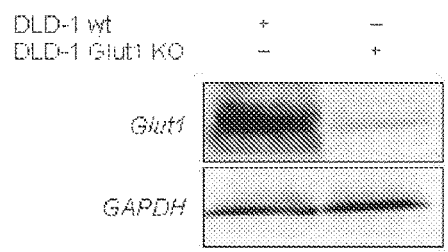
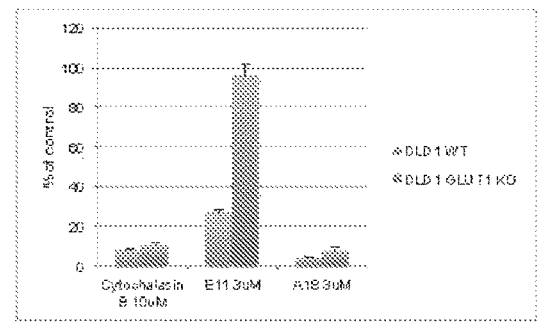
FIGURES 4A
FIGURE 4B a

| | | | | | | |
|---|---|---|---|---|---|---|
| DMSO | + | − | − | − | − | − |
| A18-S2-Biotin | − | + | + | + | + | + |
| A18 20μM | − | − | + | − | − | − |
| Rapamycin 20μM | − | − | − | + | − | − |
| SLF 20μM | − | − | − | − | + | − |
| E11 20μM | − | − | − | − | − | + |

*Glut1*

Input b

| | | | | | | |
|---|---|---|---|---|---|---|
| DMSO | + | − | − | − | − | − |
| E11-OH-Biotin | − | + | + | + | + | + |
| E11 20μM | − | − | + | − | − | − |
| Rapamycin 20μM | − | − | − | + | − | − |
| SLF 20μM | − | − | − | − | + | − |
| A18 20μM | − | − | − | − | − | + |

*Glut1*

Input

FIG. 9

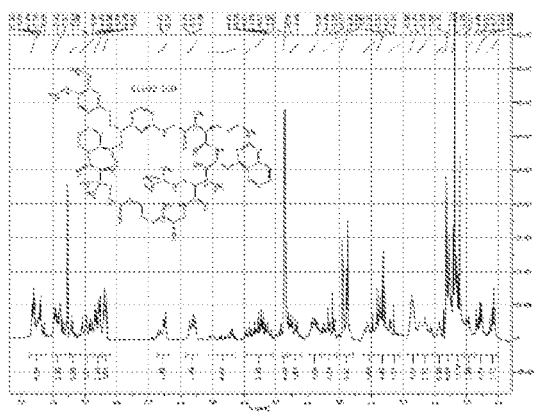 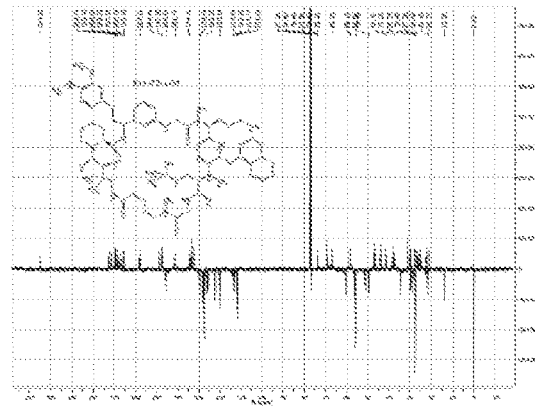
FIGURE 13A                              FIGURE 13B
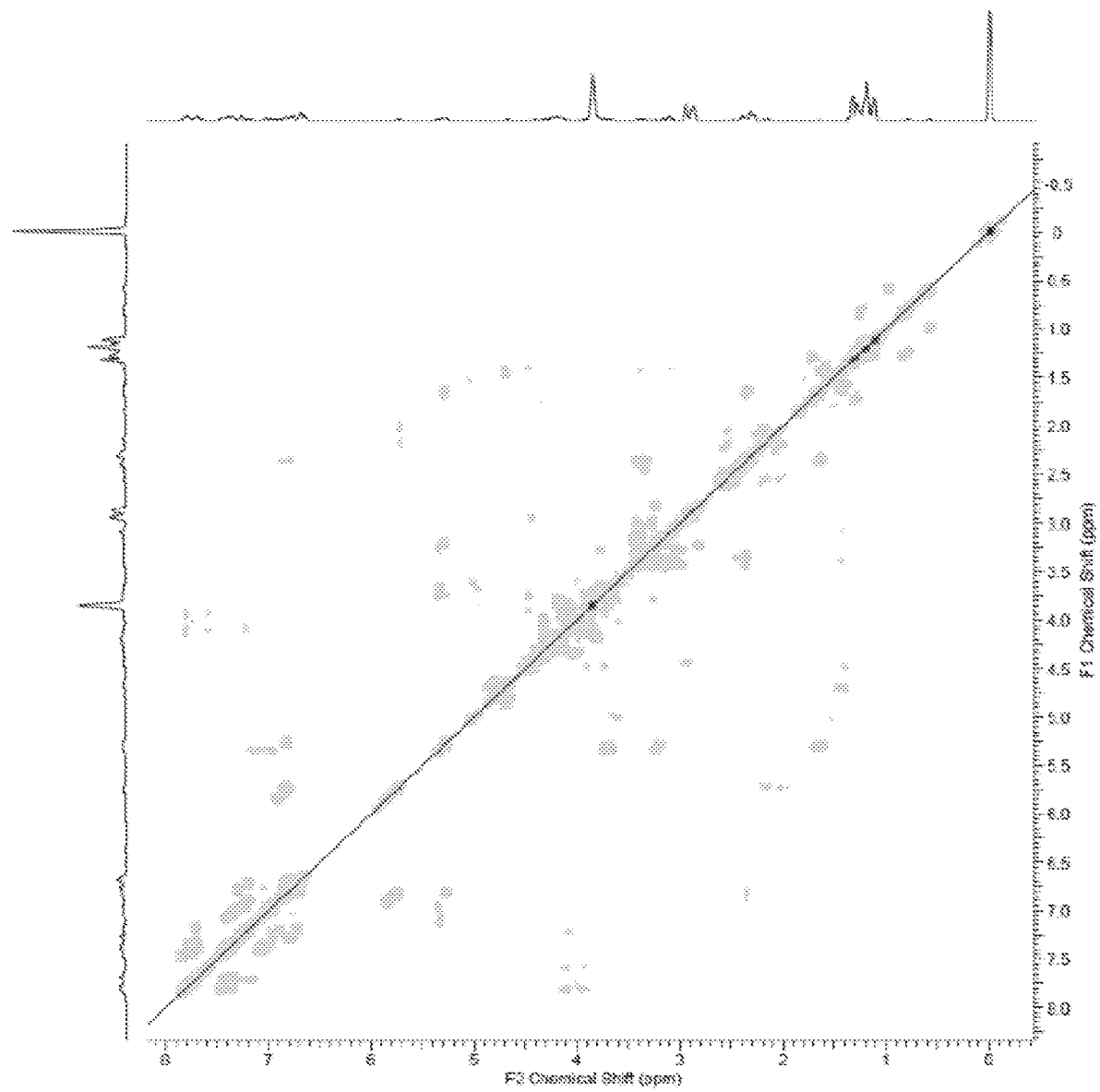
FIGURE 14

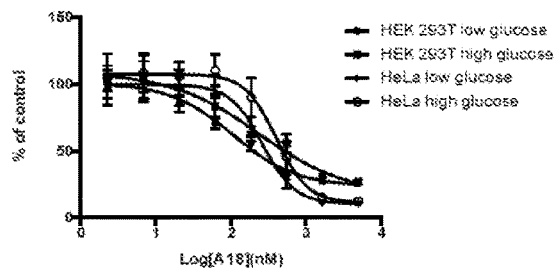 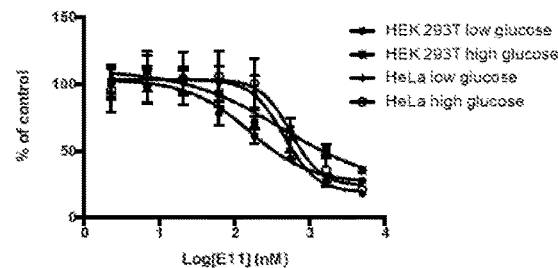
FIGURE 15A              FIGURE 15B
|              | HEK 293T LG[a] | HEK 293T HG | HeLa LG | HeLa HG |
|---|---|---|---|---|
| A18 IC50(nM) | 105.7 | 238.4 | 268.0 | 411.3 |
| E11 IC50(nM) | 159.1 | 424.4 | 458.4 | 564.8 |
a: LG indicates low glucose concentration (1g/L), HG indicates high glucose concentration (4g/L).
FIGURES 15C
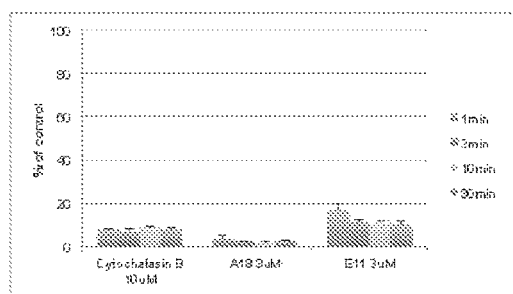 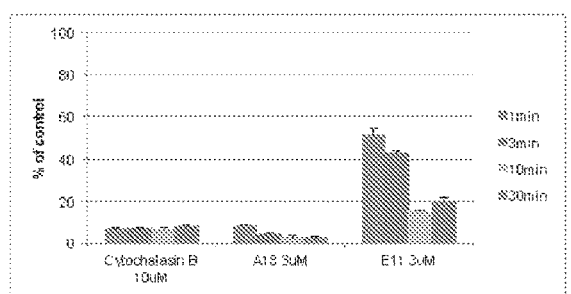
*10min drug treatment and 1/3/10/30min $^3$H-2DG uptake       *1min drug treatment and 1/3/10/30min $^3$H-2DG uptake
FIGURE 16A              FIGURE 16B

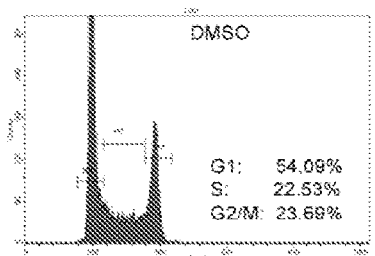
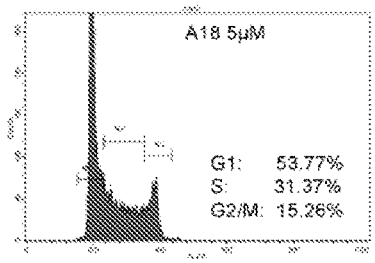
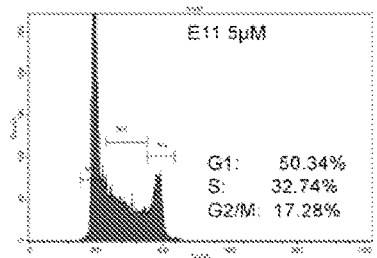
FIGURE 25A  FIGURE 25B  FIGURE 25C
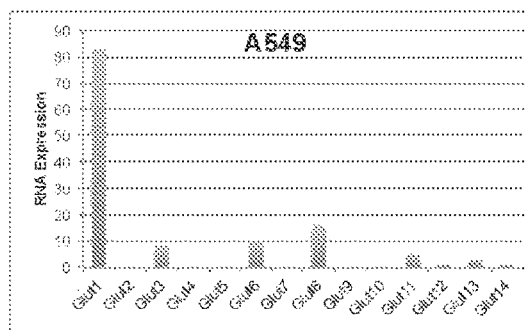
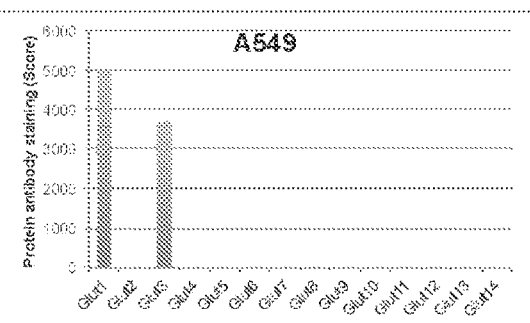
* Data from The Human Protein Atlas project website
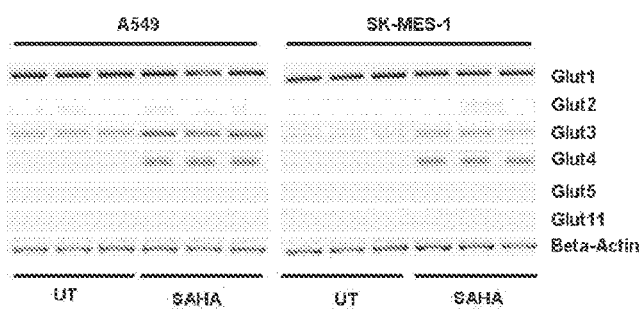
Cancers 2011, 3, 1550-1565
FIGURE 26

RAPAGLUTINS, NOVEL INHIBITORS OF GLUT AND USE THEREOF

CROSS-REFERENCE TO RELATED APPLICATIONS

This application is a 35 USC § 371 National Stage application of International Application No. PCT/US2017/016516 filed Feb. 3, 2017, now pending; which claims the benefit under 35 USC § 119(e) to U.S. Application Ser. No. 62/291,453 filed Feb. 4, 2016. The disclosure of each of the prior applications is considered part of and is incorporated by reference in the disclosure of this application.

GRANT INFORMATION

This invention was made with government support under National Institutes of Health grant DP1CA174428. The government has certain rights in the invention.

BACKGROUND OF THE INVENTION

Field of the Invention

The invention relates generally to inhibitors of cell proliferation and more specifically to rapafucin chemical compounds useful for the treatment of cancer.

Background Information

Glucose is the main source of energy in eukaryotic organisms and plays a central role in metabolism and cellular homeostasis. Glucose transporters are a wide group of membrane proteins that facilitate the transport of glucose over a plasma membrane. Because tumors are fast growing, they need the proteins that carry nutrients into the cells to function at full capacity. Therefore, an important strategy for cancer treatment would be to block these proteins. Since the GLUT family is one of the major group of membrane transport proteins that transport glucose and other substances into cells, inhibiting these proteins should be important in stopping the spread of cancer. In addition, GLUT also plays a key role in T lymphocyte activation. Inhibition of glucose transport can modulate immune response and have implication in the treatment of a wide variety of immune related diseases from graft rejection to various autoimmune diseases.

SUMMARY OF THE INVENTION

The present invention is based on the seminal discovery of rapafucin compounds that inhibit cell proliferation and T cell activation.

In one embodiment, the invention provides a method of treating cancer in a subject comprising administering to the subject an anti-proliferative effective amount of any one of the following compounds:

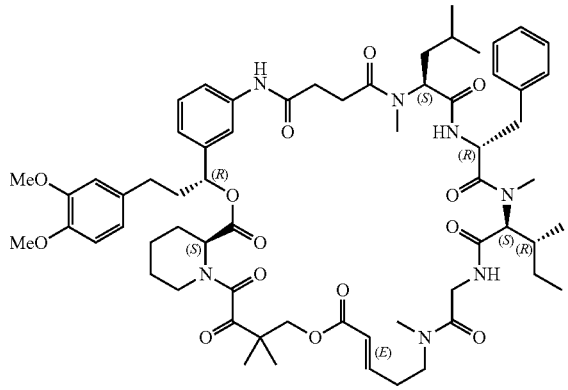

A18

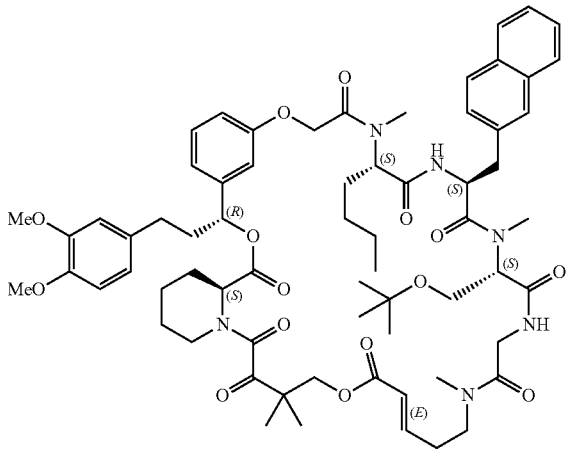

E11

| A18-2 | $^M$Gly-$^M$Ile-$^D$Phe-$^M$Leu |
| A18-3 | Pro-$^M$Ile-$^D$Phe-$^M$Leu |
| A18-4 | $^D$Pro-$^M$Ile-$^D$Phe-$^M$Leu |
| A18-5 | Gly-$^M$Val-$^D$Phe-$^M$Leu |
| A18-6 | Gly-$^M$Ie-$^D$Phe-$^M$Leu |
| A18-7 | Gly-$^M$Phg-$^D$Phe-$^M$Leu |
| A18-8 | Gly-$^M$Nle-$^D$Phe-$^M$Leu |
| A18-9 | Gly-$^M$Nva-$^D$Phe-$^M$Leu |
| A18-10 | Gly-$^M$Leu-$^D$Phe-$^M$Leu |
| A18-11 | Gly-$^M$Ile-$^D$hoPhe-$^M$Leu |
| A18-12 | Gly-$^M$Ile-$^D$Pyr-$^M$Leu |
| A18-13 | Gly-$^M$Ile-$^D$PhdiCl-$^M$Leu |
| A18-14 | Gly-$^M$Ile-$^D$Tyr-$^M$Leu |
| A18-15 | Gly-$^M$Ile-$^{MD}$Phe-$^M$Leu |
| A18-16 | Gly-$^M$Ile-$^D$Leu-$^M$Leu |
| A18-17 | Gly-$^M$Ile-$^D$phe-Leu |
| A18-18 | Gly-$^M$Ile-$^D$Phe-$^M$Ile |
| A18-19 | Gly-$^M$Ile-$^D$Phe-$^M$Nva |
| A18-20 | Gly-$^M$Ile-$^D$Phe-$^M$Nle |
| A18-21 | Gly-$^M$Ile-$^D$Phe-$^M$Val |
| A18-22 | Gly-$^M$Ile-$^D$Phe-$^M$Phe |
| E11-72-1 | Gly-$^M$SerBu-Nal-$^M$Ala |
| E11-72-2 | $^M$Gly-$^M$SerBu-Nal-$^M$Ala |
| E11-72-3 | Gly-$^M$Ser-Nal-$^M$Ala |
| E11-72-4 | Gly-HoSMe-Nal-$^M$Ala |
| E11-72-5 | Gly-$^M$SerBu-$^M$Phe-$^M$Ala |
| E11-72-6 | Gly-$^M$SerBu-Phe-$^M$Ala |
| E11-72-7 | Gly-$^M$SerBu-Phl-$^M$Ala |
| E11-72-8 | Gly-$^M$SerBu-PheCl-$^M$Ala |
| E11-72-9 | Gly-$^M$SerBu-hoPhe-$^M$Ala |
| E11-72-10 | Gly-$^M$SerBu-Fur-$^M$Ala |
| E11-72-12 | Gly-$^M$SerBu-TyrOMe-$^M$Ala |
| E11-71-13 | Gly-$^M$SerBu-biPhe-$^M$Ala |

-continued

| | |
|---|---|
| E11-71-14 | Gly-$^M$SerBu-PhCF3-$^M$Ala |
| E11-71-15 | Gly-$^M$SerBu-PhpMe-$^M$Ala |
| E11-71-16 | Gly-$^M$SerBu-Nal-Ala |
| E11-71-17 | $^D$Pro-$^M$SerBu-Nal-$^M$Ala |
| E11-71-18 | Pro-$^M$SerBu-Nal-$^M$Ala |
| E11-71-19 | Gly-$^M$Leu-Nal-$^M$Ala |
| E11-71-20 | Gly-$^M$Phe-Nal-$^M$Ala |
| E11-71-21 | Gly-$^M$TyrBu-Nal-$^M$Ala |
| E11-71-22 | Gly-$^M$SerBu-TyrBu-$^M$Ala |
| E11-71-23 | Gly-$^M$SerBu-PhN-$^M$Ala |
| E11-71-24 | Gly-$^M$SerBu-Nal-$^M$Gly |
| E11-71-25 | Gly-$^M$SerBu-Nal-$^{MD}$Ala |
| E11-71-26 | Gly-$^M$SerBu-Nal-Pro |
| E11-71-27 | Gly-$^M$SerBu-Nal-$^M$Nva |
| E11-71-28 | Gly-$^M$SerBu-Nal-$^M$Phe |
| E11-71-29 | Gly-$^M$SerBu-Nal-$^M$Leu |
| E11-71-30 | Gly-$^M$SerBu-Nal-$^M$Ile |
| E11-71-31 | Gly-$^M$SerBu-Nal-$^M$Nle |
| E11-71-31-2 | Gly-$^M$SerBu-Phl-$^M$Nle |
| E11-71-31-3 | Gly-$^M$SerBu-PhCF3-$^M$Nle |
| E11-71-31-4 | Gly-$^M$SerBu-TyrBu-$^M$Nle |
| E11-71-31-5 | Gly-$^M$SerBu-biPhe-$^M$Nle |
| E11-71-31-6 | Gly-$^M$SerBu-hoPhe-$^M$Nle |
| E11-71-31-7 | Gly-$^M$SerBu-mTyrBu-$^M$Nle |

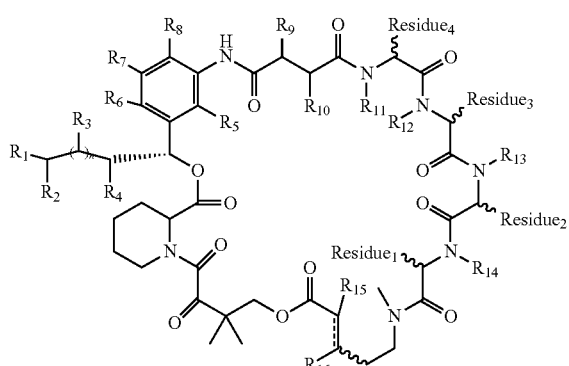

n=0-6

$R_1$:

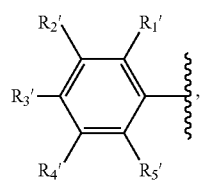

Wherein $R_1'$-$R_5'$=OH, NH$_2$, SH, CN, H, OAc, or OMe individually or in combination,

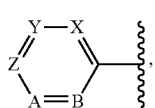

Wherein: A, B, X, Y, Z=C, N, or P either individually or in combination,

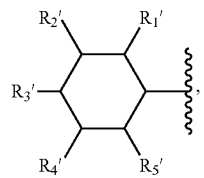

Wherein $R_1'$-$R_5'$=OH, NH$_2$, SH, H, OAc, OMe individually or in combination,

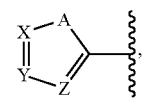

Wherein A, X, Y, or Z=CHn' (n'=0-2), O, N, S, whenever appropriate, individually or in combination, $R_2$-$R_4$: H, methyl, ethyl, propyl, isopropyl, phenyl, OH, NH$_2$, SH, CN, individually or in combination, $R_5$-$R_8$: methyl, ethyl, propyl, isopropyl, phenyl, OH, NH$_2$, SH, CN, individually or in combination, $R_9$=OH, NH$_2$, SH, CN, H;

$R_{10}$=OH, NH$_2$, SH, CN, H;

$R_{11-14}$=H or Me;

$R_{15}$=OH, NH$_2$, SH, CN, H;

$R_{16}$=OH, NH$_2$, SH, CN, H.

The bond between the carbons bearing $R_{15}$ and $R_{16}$ can be either a single or a double bond in either E or Z configuration.

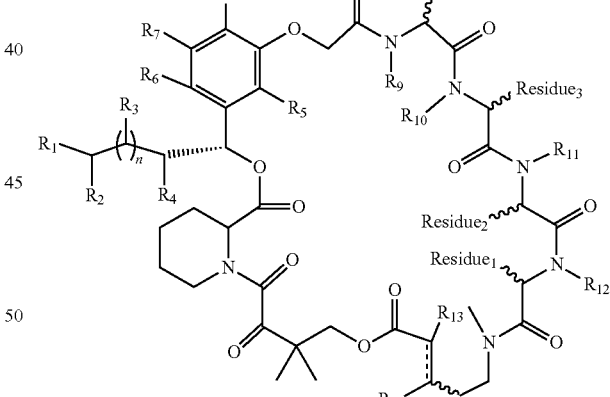

n=0-6

$R_1$:

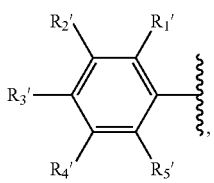

Wherein R$_1$'-R$_5$'=OH, NH$_2$, SH, CN, H, OAc, or OMe individually or in combination,

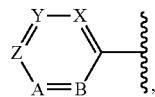

Wherein: A, B, X, Y, Z=C, N, or P either individually or in combination,

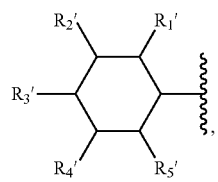

Wherein R$_1$'-R$_5$'=OH, NH$_2$, SH, H, OAc, OMe individually or in combination,

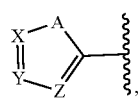

Wherein A, X, Y, or Z=CHn' (n'=0-2), O, N, S, whenever appropriate, individually or in combination, R$_2$-R$_4$: H, methyl, ethyl, propyl, isopropyl, phenyl, OH, NH$_2$, SH, CN, individually or in combination, R$_5$-R$_8$: methyl, ethyl, propyl, isopropyl, phenyl, OH, NH$_2$, SH, CN, individually or in combination, R$_{9-12}$=H or Me.

R$_{13}$=OH, NH$_2$, SH, CN, H;

R$_{14}$=OH, NH$_2$, SH, CN, H.

The bond between the carbons bearing R$_{13}$ and R$_{14}$ can be either a single or a double bond in either E or Z configuration.

wherein residues 1-4 can be any amino acid building block listed below or version.

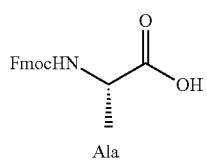
Ala

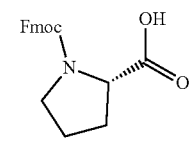
Pro

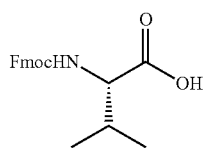
Val

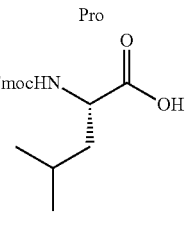
Leu

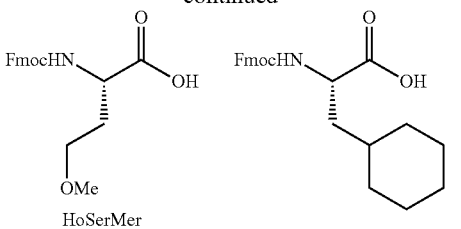
HoSerMer  ChA

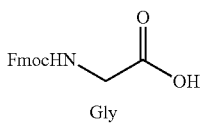
Gly

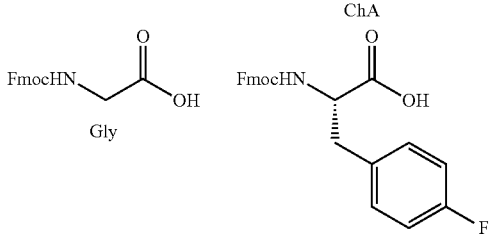
PhF

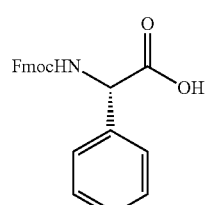
PhG  dLeu

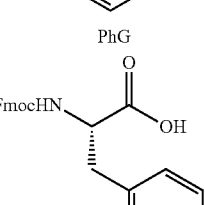
Phe

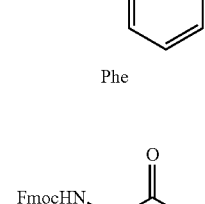
NaI

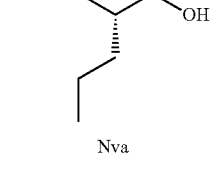
Nva  dAla

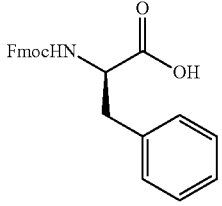
dPhe  mGly

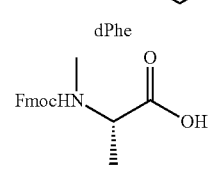
mAla  mLeu

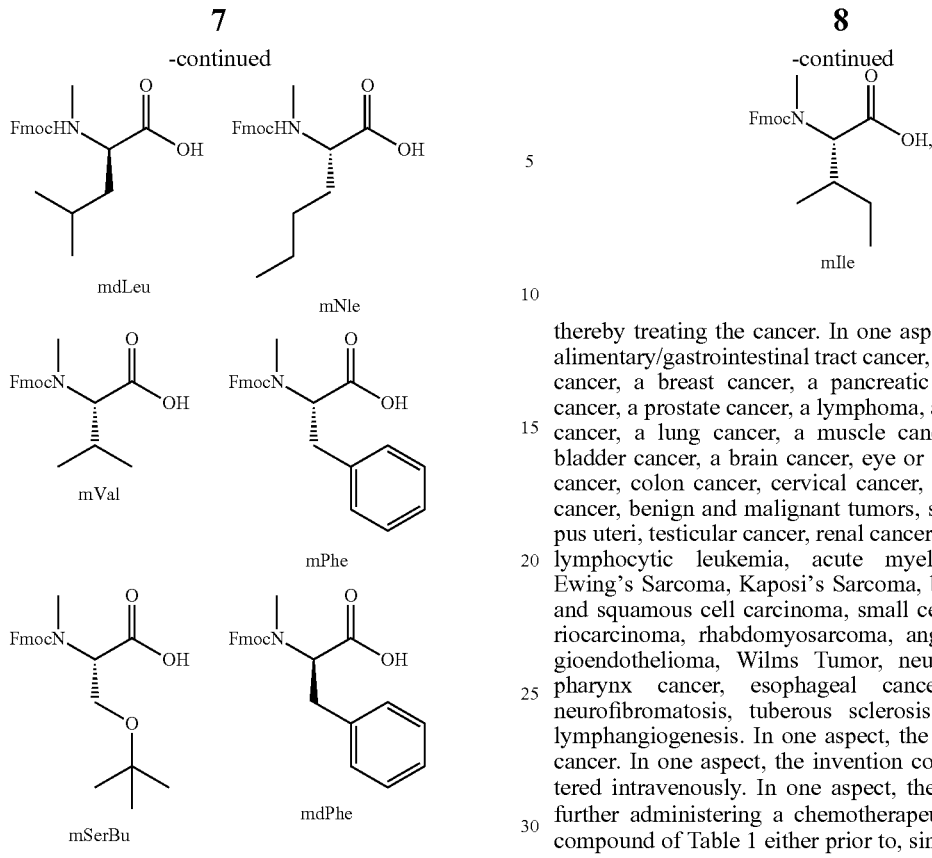

thereby treating the cancer. In one aspect, the cancer is an alimentary/gastrointestinal tract cancer, a liver cancer, a skin cancer, a breast cancer, a pancreatic cancer, an ovarian cancer, a prostate cancer, a lymphoma, a leukemia, a kidney cancer, a lung cancer, a muscle cancer, a bone cancer, bladder cancer, a brain cancer, eye or ocular cancer, rectal cancer, colon cancer, cervical cancer, bladder cancer, oral cancer, benign and malignant tumors, stomach cancer, corpus uteri, testicular cancer, renal cancer, throat cancer, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, neurofibromatosis, tuberous sclerosis, hemangiomas, or lymphangiogenesis. In one aspect, the cancer is metastatic cancer. In one aspect, the invention compound is administered intravenously. In one aspect, the invention provides further administering a chemotherapeutic compound or a compound of Table 1 either prior to, simultaneously with or following administration of an invention compound.

TABLE 1

| | Inhibitors of glucose transporters | | |
|---|---|---|---|
| Compound Name | Structure | $IC_{50}$ (cell line) | Ref. |
| Phloretin | 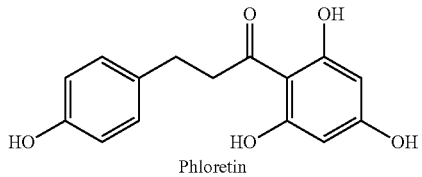 Phloretin | >10 µM (SW620) | *Cancer Chemother. Pharmacol.* 2007 |
| Cytochalasin B | 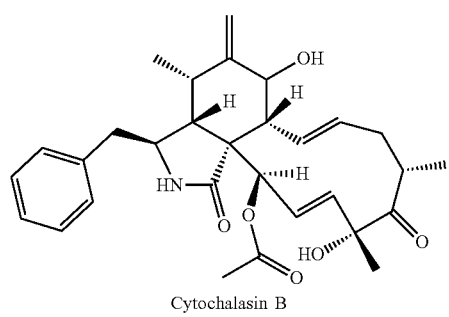 Cytochalasin B | 1 µM (NISI-67) | *Proc. Nat. Acad. Sci. USA* 1972 |

TABLE 1-continued

Inhibitors of glucose transporters

| Compound Name | Structure | IC$_{50}$ (cell line) | Ref. |
|---|---|---|---|
| WZB117 | WZB117 | ~0.5 μM (A549) | *Mol. Cancer Ther.* 2012 |
| Fasentin | Fasentin | ~80 μM (DU145) | *Mol. Cancer Ther.* 2008 |
| Genistein | Genistein | ~12 μM (HL-60) | *J. Biol. Chem.* 1996 |
| STF-31 | STF-31 | ~1.2 μM (RCC4) | *Sci. Transl. Med.* 2011 |
| Compound 11 | Compound 11 | 2 μM (CHO-K1) | *Chem. Biol.* 2010 |

TABLE 1-continued

Inhibitors of glucose transporters

| Compound Name | Structure | IC$_{50}$ (cell line) | Ref. |
|---|---|---|---|
| Cpd30 | 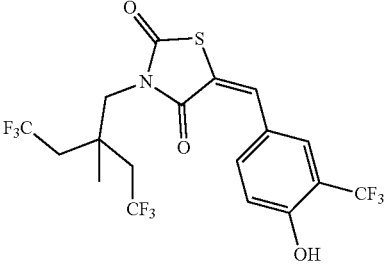 [SMILES: CC(CN1C(=O)S/C(=C/c2ccc(O)c(C(F)(F)F)c2)C1=O)(CC(F)(F)F)CC(F)(F)F]<br>Cpd30 | 2 μM (LNCaP) | J. Med. Chem. 2012 |

In another embodiment, the above compounds can be used to treat possible organ rejection in subjects receiving an organ transplant.

In another embodiment, the above compounds can be used to treat autoimmune diseases.

An isolated compound from the above compounds is included in one embodiment of the invention. Further, a method of synthesizing a compound Formula A18 or E11 shown in FIG. 1a comprising synthetic scheme I or II is included in one embodiment. Further, a pharmaceutical composition comprising an invention compound is included in the invention.

Scheme I

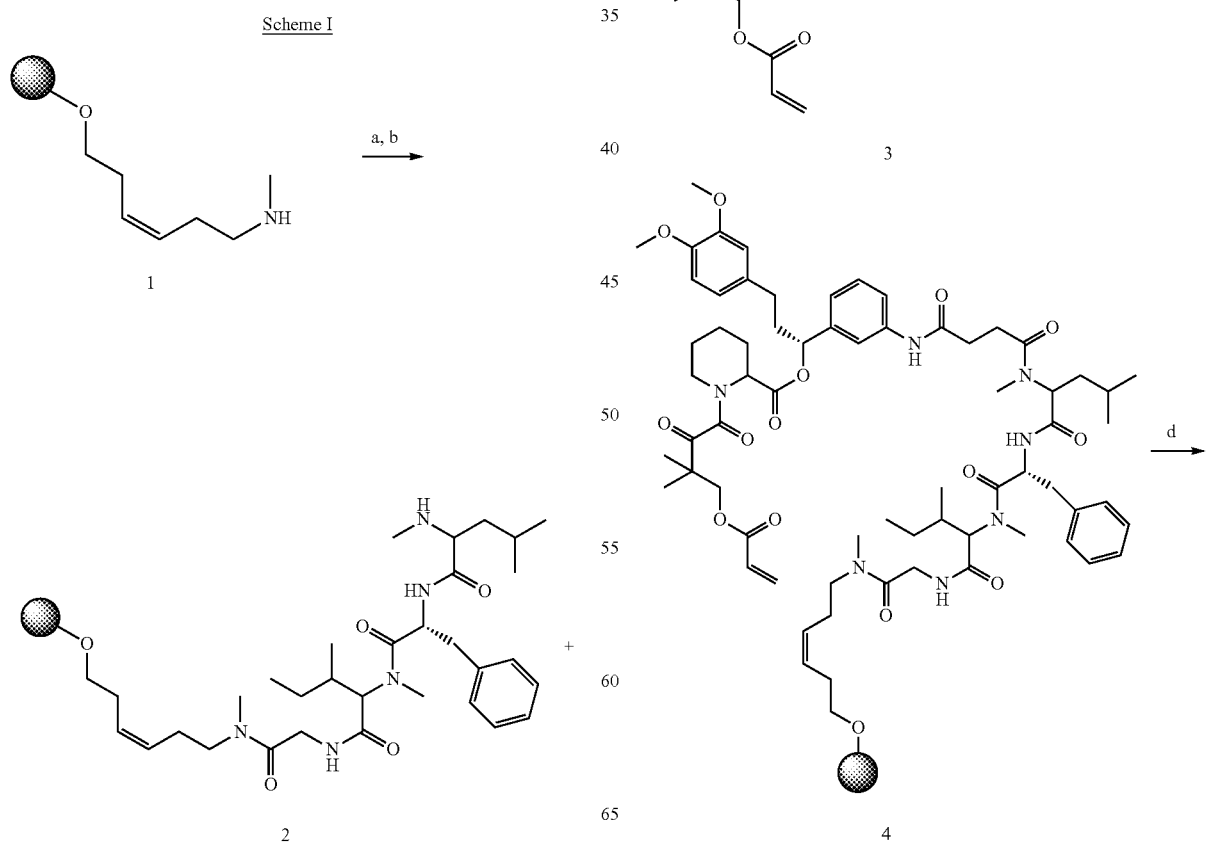

13
-continued
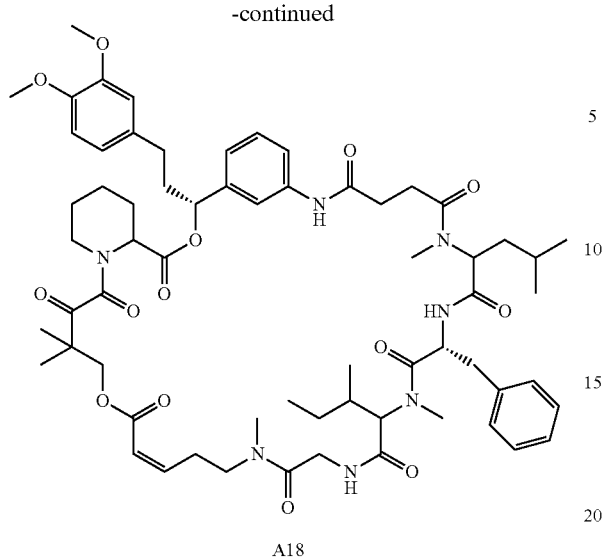
A18
Synthesis of A18. Reagents and Conditions: (a) Fmoc-AA-OH, HATU, DIPEA, DMF, RT, 2 h; (b) 20% Piperidine, DMF, RT, 30 min; (c) HATU, DIPEA, DMF, RT, 2 h; (d) Hoveyda-Grubbs catalyst 2nd generation (30 mol %), 1,2-dichloroethane, 140° C. microwave, 30 min.
14
-continued
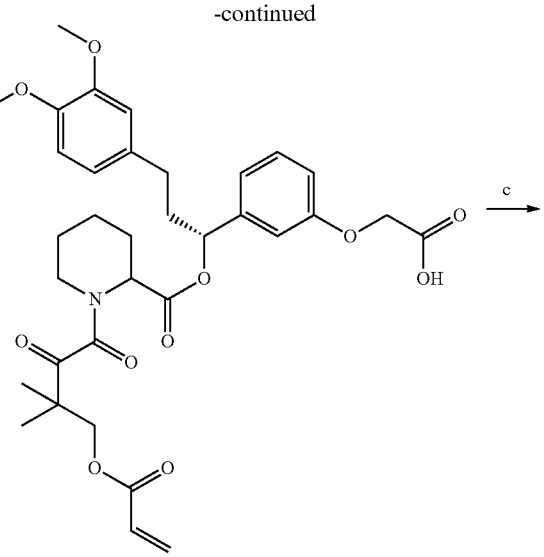
3
Scheme II
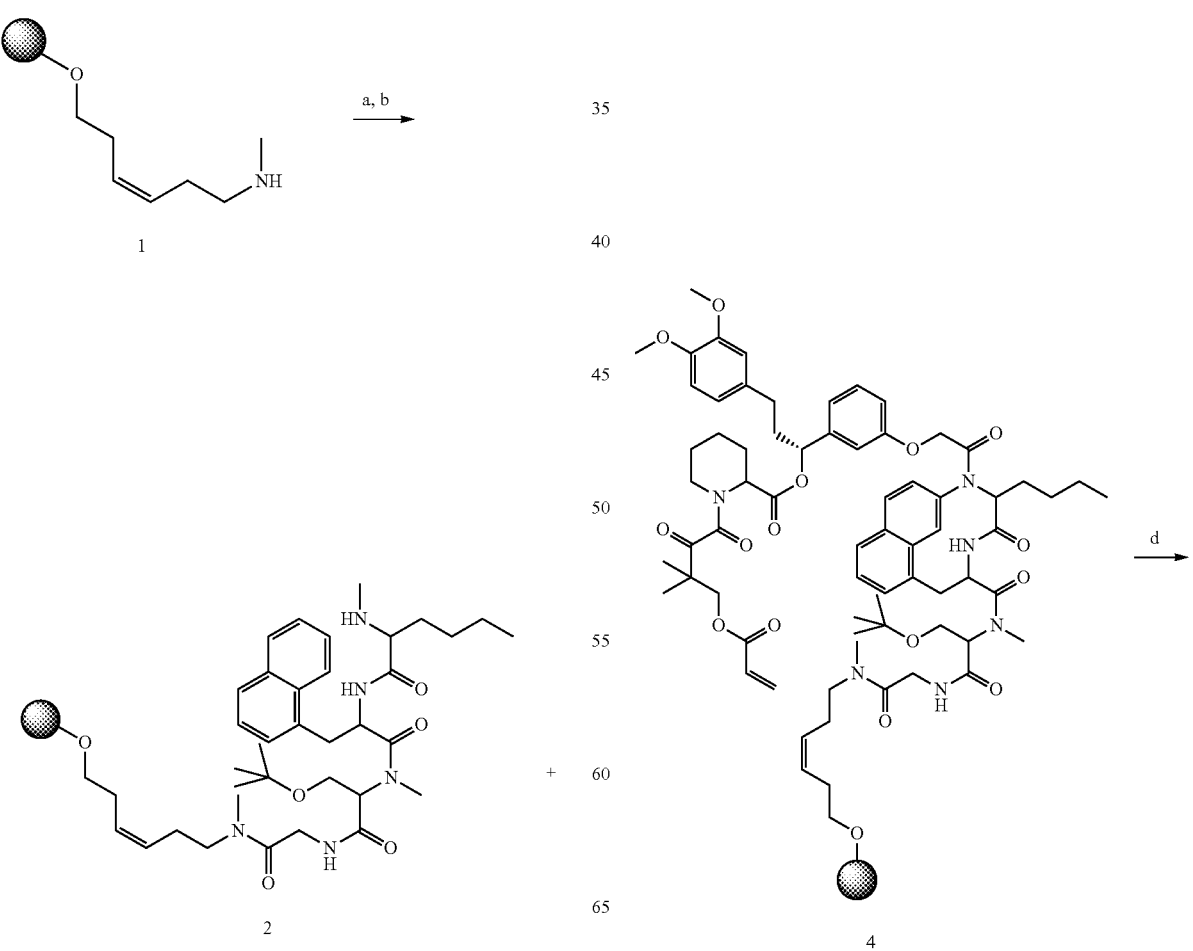

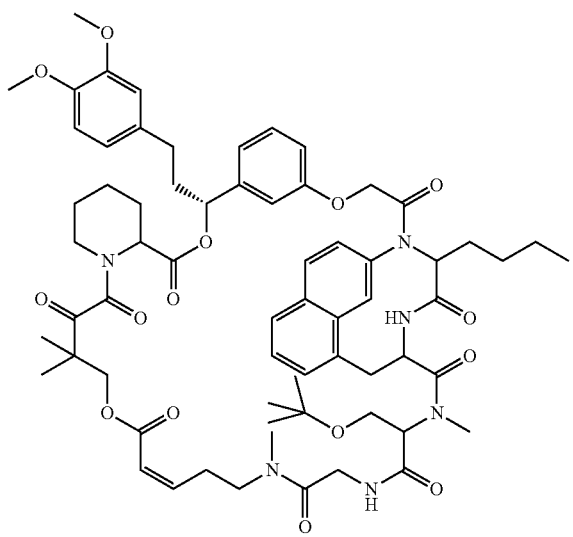

E11

Synthesis of E11. Reagents and Conditions: (a) Fmoc-AA-OH, HATU, DIPEA, DMF, RT, 2 h; (b) 20% Piperidine, DMF, RT, 30 min; (c) HATU, DIPEA, DMF, RT, 2 h; (d) Hoveyda-Grubbs catalyst 2nd generation (30 mol %), 1,2-dichloroethane, 140° C. microwave, 30 min.

Additional compounds that can be used to treat cancer, autoimmune disease and possible organ rejection are represented by the following generic structure:

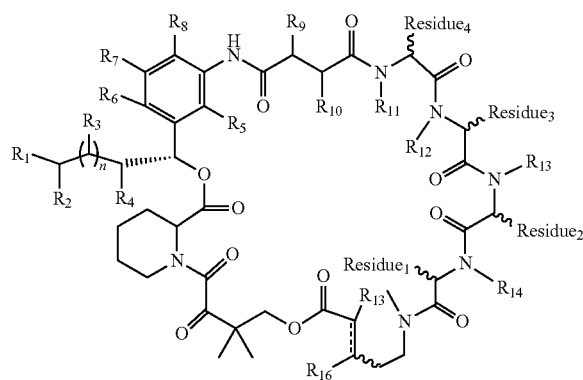

n=0-6
$R_1$:

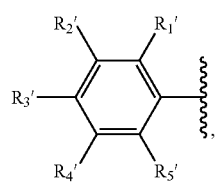

Wherein $R_1'$-$R_5'$=OH, $NH_2$, SH, CN, H, OAc, or OMe individually or in combination,

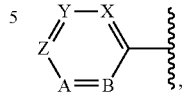

Wherein: A, B, X, Y, Z=C, N, or P either individually or in combination,

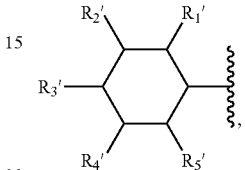

Wherein $R_1'$-$R_5'$=OH, $NH_2$, SH, H, OAc, OMe individually or in combination,

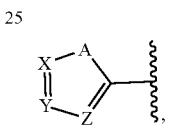

Wherein A, X, Y, or Z=CHn' (n'=0-2), O, N, S, whenever appropriate, individually or in combination,
$R_2$-$R_4$: H, methyl, ethyl, propyl, isopropyl, phenyl, OH, $NH_2$, SH, CN, individually or in combination,
$R_5$-$R_8$: methyl, ethyl, propyl, isopropyl, phenyl, OH, $NH_2$, SH, CN, individually or in combination,
$R_9$=OH, $NH_2$, SH, CN, H;
$R_{10}$=OH, $NH_2$, SH, CN, H;
$R_{11-14}$=H or Me;
$R_{15}$=OH, $NH_2$, SH, CN, H;
$R_{16}$=OH, $NH_2$, SH, CN, H.

The bond between the carbons bearing $R_{15}$ and $R_{16}$ can be either a single or a double bond in either E or Z configuration.

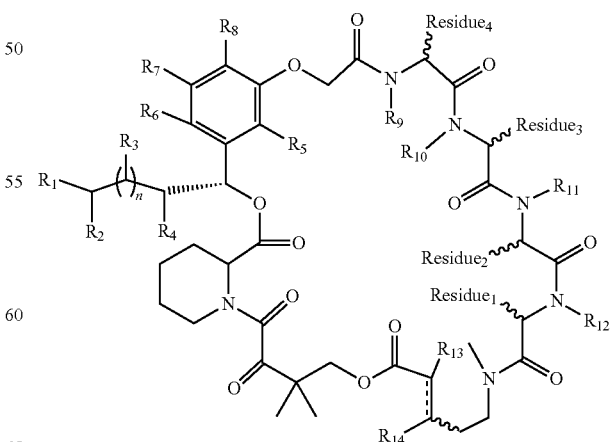

n=0-6
R₁:

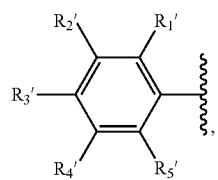

Wherein R₁'-R₅'=OH, NH₂, SH, CN, H, OAc, or OMe individually or in combination,

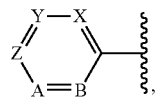

Wherein: A, B, X, Y, Z=C, N, or P either individually or in combination,

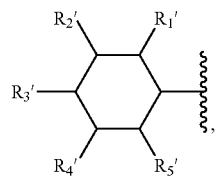

Wherein R₁'-R₅'=OH, NH₂, SH, H, OAc, OMe individually or in combination,

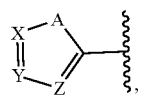

Wherein A, X, Y, or Z=CHn' (n'=0-2), O, N, S, whenever appropriate, individually or in combination,
R₂-R₄: H, methyl, ethyl, propyl, isopropyl, phenyl, OH, NH₂, SH, CN, individually or in combination,
R₅-R₈: methyl, ethyl, propyl, isopropyl, phenyl, OH, NH₂, SH, CN, individually or in combination,
$R_{9-12}$=H or Me.
$R_{13}$=OH, NH₂, SH, CN, H;
$R_{14}$=OH, NH₂, SH, CN, H.
The bond between the carbons bearing $R_{13}$ and $R_{14}$ can be either a single or a double bond in either E or Z configuration.
Residues 1-4 can be any amino acid building block listed in Table 1 or its modified version.

TABLE 2

Amino Acid Building Blocks for Residues in the Effector Domain

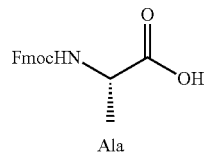

Ala

TABLE 2-continued

Amino Acid Building Blocks for Residues in the Effector Domain

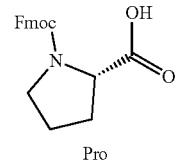

Pro

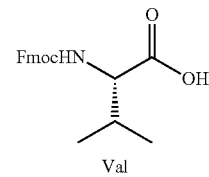

Val

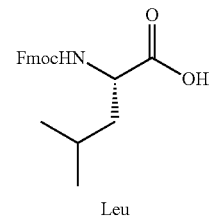

Leu

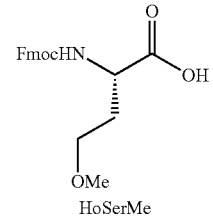

HoSerMe

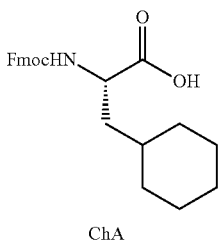

ChA

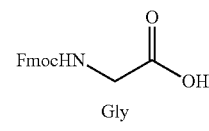

Gly

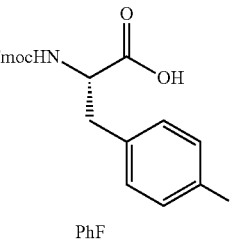

PhF

TABLE 2-continued
Amino Acid Building Blocks for Residues in the Effector Domain
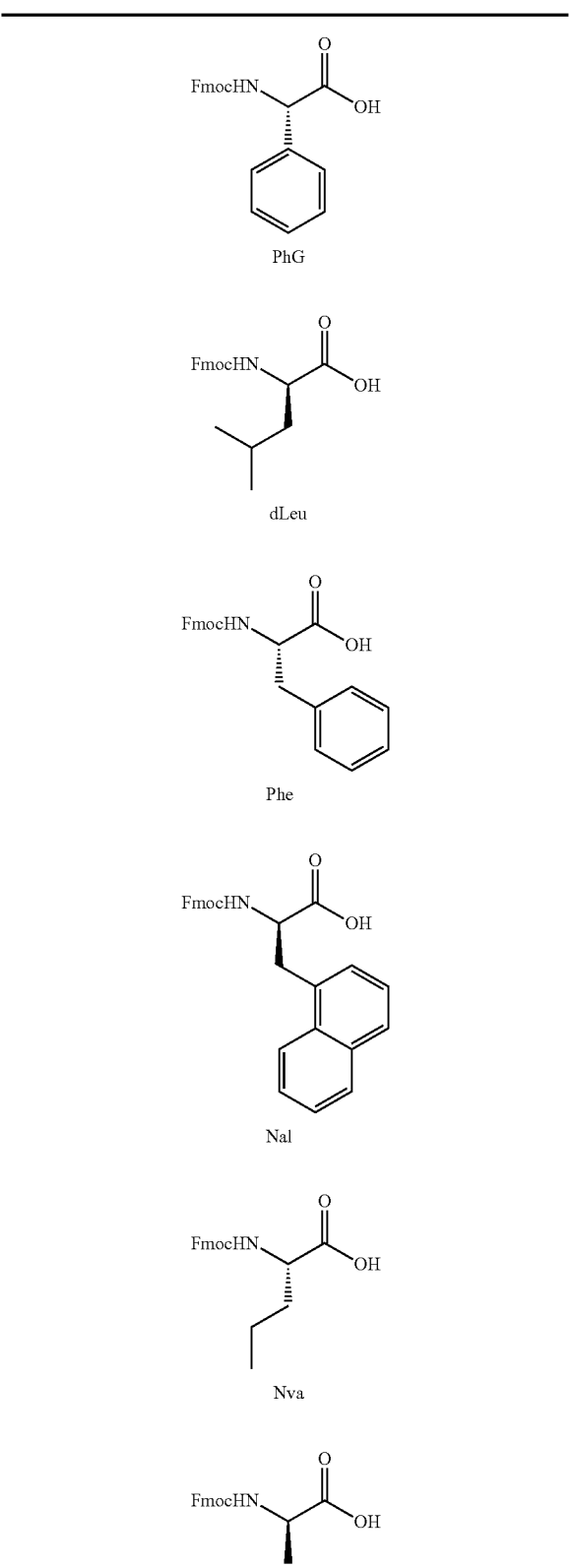
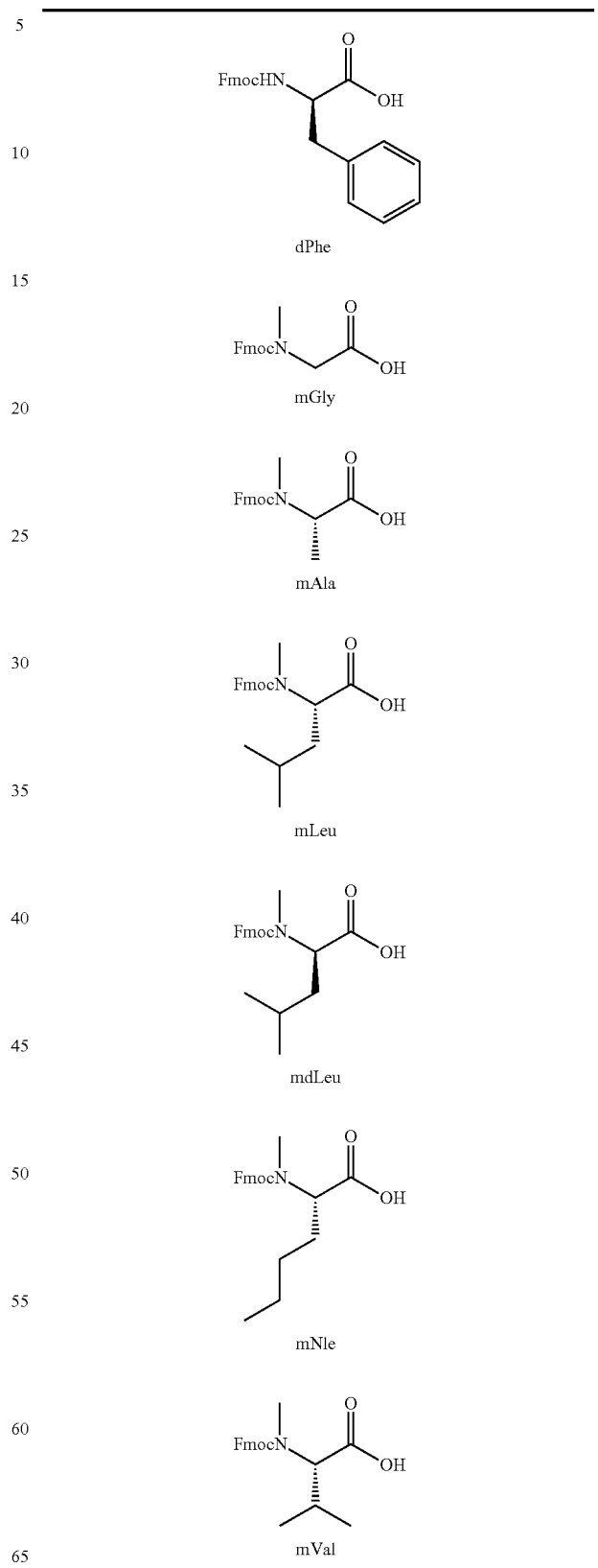

TABLE 2-continued

Amino Acid Building Blocks for Residues in the Effector Domain

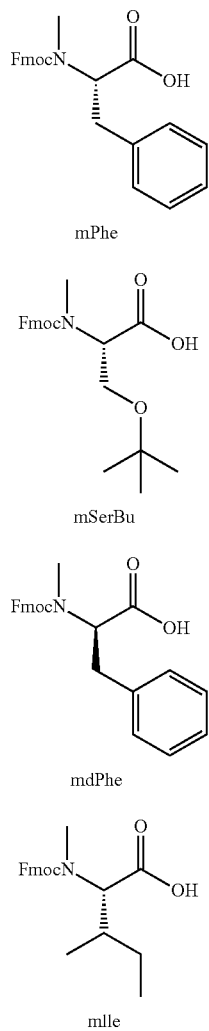

mPhe mSerBu mdPhe mIle

BRIEF DESCRIPTION OF THE DRAWINGS

FIGS. 3A-3D. Inhibition of Glucose Transport by A18 and E11. (a) Inhibition of 3-O-methyl-D-[3H] glucose uptake in human red blood cells by A18. (b) Inhibition of 3-O-methyl-D-[3H] glucose uptake in human red blood cells by E11. (c) Inhibition of 3-O-methyl-D-[3H] glucose uptake in erythrocyte ghosts by A18. (d) Inhibition of 3-O-methyl-D-[3H] glucose uptake in erythrocyte ghosts by E11.

FIGS. 4A-4B. E11 is a specific inhibitor of Glut1. (a) Glut1 protein levels of DLD-1 wild type and knock out cells analyzed by western blotting. (b) Inhibition of 2-deoxy-D-[3H] glucose uptake in DLD-1 wild type and knock out cells by E11 or A18.

FIGS. 13A-13B. 1H-NMR (a) and 13C-NMR (b) of E11.
FIG. 14. 2D COSY NMR of E11.

FIGS. 15A-15C. High concentration of glucose slightly reverses A18 and E11's anti-proliferation effect. (a)(b) Inhibition of cell proliferation by A18 and E11 in cancer cells cultured under different glucose concentrations. (c) Detailed IC50 values of A18 and E11 from (a) and (b). Potency of A18 and E11 against the alamar blue assay on cancer cell lines cultured under different glucose concentrations.

FIGS. 16A-16B. Inhibition of Glucose Transport by A18 and E11. Cytochalasin B (10 μM), A18 (3 μM), E11 (3 μM) and DMSO control were used to treated A549 cells for 10 min (a) or 1 min (b), then glucose uptake in the treated cells was measured at 1, 3, 10 and 30 min after the addition of 2-dexoy-D-[$^3$H] glucose.

FIGS. 25A-25C. A18 and E11 inhibit cell cycle progression in the S phase. HEK 293T were incubated with DMSO (a), 5 µM A18 (b) or 5 µM E11 (c) for 24 h before they were harvested for cell cycle analysis.

FIG. 26. Over-expression of Glut1 and Glut3 in A549 lung cancer cells.

DETAILED DESCRIPTION OF THE INVENTION

The present invention is based on the identification of novel inhibitors of cellular proliferation.

As used herein, a "therapeutically effective amount" of a compound, is the quantity of a compound which, when administered to an individual or animal, results in a sufficiently high level of that compound in the individual or animal to cause a discernible inhibition of cellular proliferation. The exact dosage and frequency of administration depends on the particular compound of the invention used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines. The term "pharmaceutically acceptable salts" refers to physiologically and pharmaceutically acceptable salts of the compounds of the invention, e.g., salts that retain the desired biological activity of the parent compound and do not impart undesired toxicological effects thereto.

As used herein, the term "cancer" or "cancerous growth" means the uncontrolled, abnormal growth of cells and includes within its scope all the well-known diseases that are caused by the uncontrolled and abnormal growth of cells. Non-limiting examples of common cancers include bladder cancer, breast cancer, ovarian cancer, pancreatic cancer, and gastric cancer, cervical cancer, colon cancer, endometrial cancer, head and neck cancer, lung cancer, melanoma, multiple myeloma, leukemia (e.g., myeloid, lymphocytic, myelocytic and lymphoblastic leukemias), non-hodgkin's lymphoma, prostate cancer, rectal cancer, and malignant melanomas.

In addition to invention compounds, one of skill in the art would recognize that chemotherapeutic agents can be used prior to, simultaneously with or following treatment with invention compounds. Illustrative agents include but are not limited to, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic antibodies or other proteins are also envisioned in combination therapies of the invention.

The following examples are intended to illustrate but not limit the invention.

Example 1

Figures 1A, 1B, 1C:
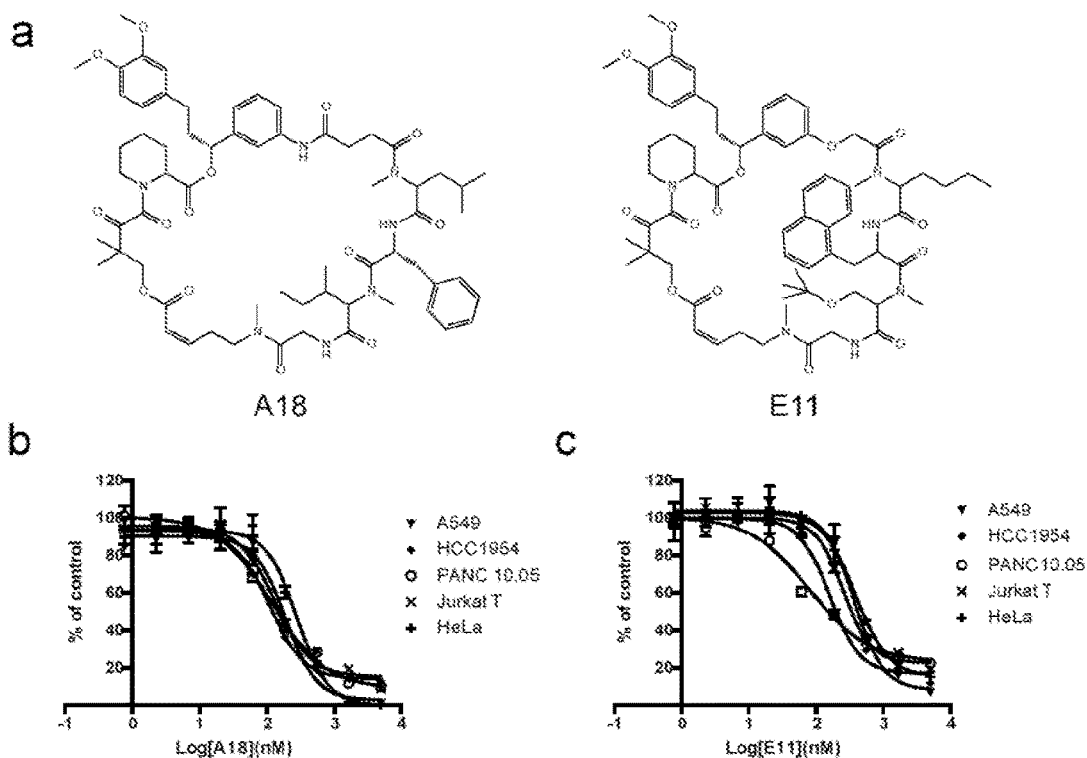
FIGS. 1A-1C. A18 and E11 are potent cell proliferation inhibitors. (a) Chemical structures of A18 and E11. (b) Inhibition of cell proliferation in different cancer cells by A18. (c) Inhibition of cell proliferation in different cancer cells by E11.
Figure 9:
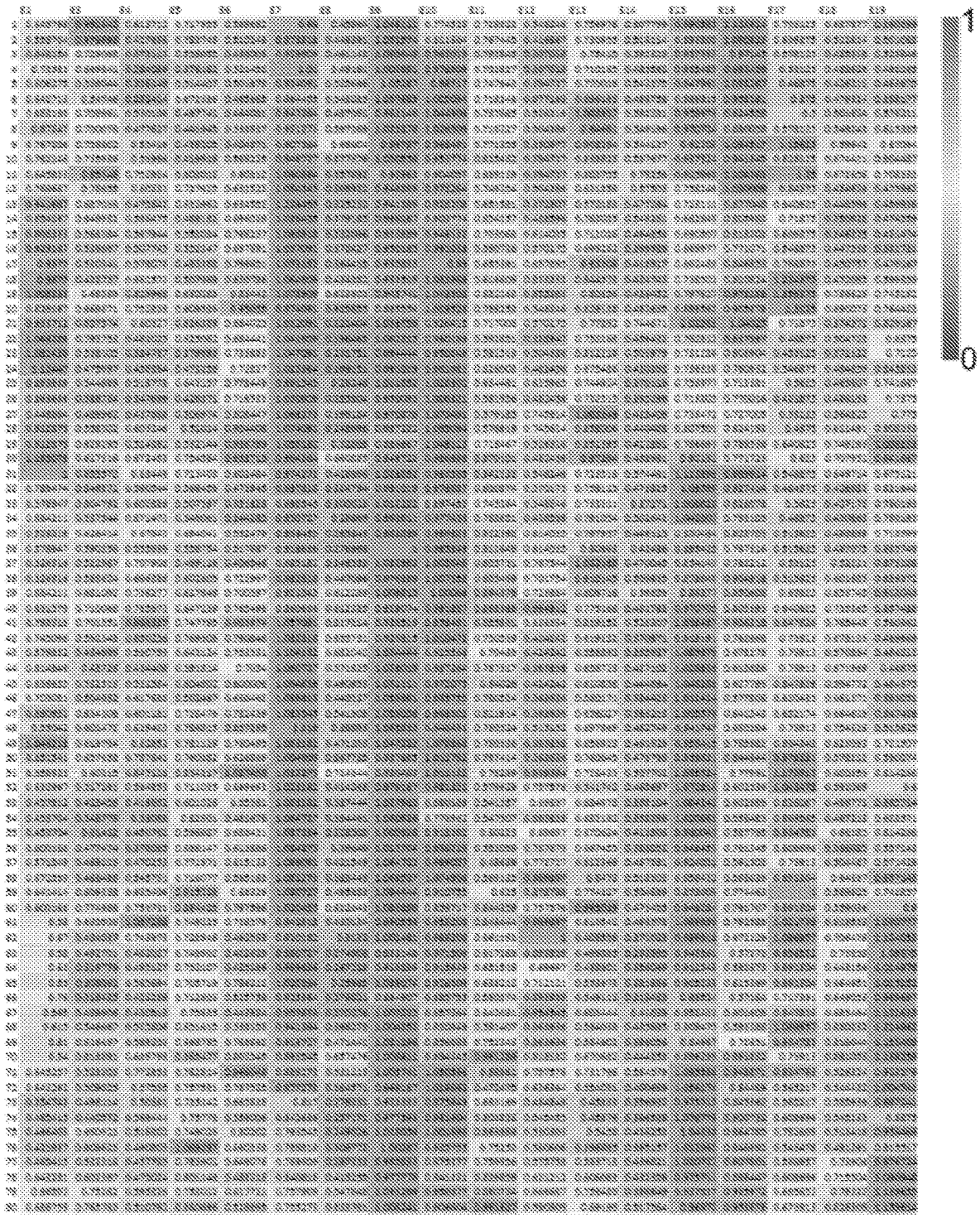
FIG. 9. Heat map of the screening results. Scale: 0 (red), complete inhibition; 1 (green), no inhibition. Screening of the rapafucin library for toxicity hits against A549 lung cancer cells using alamar blue assay.
Figure 10A:
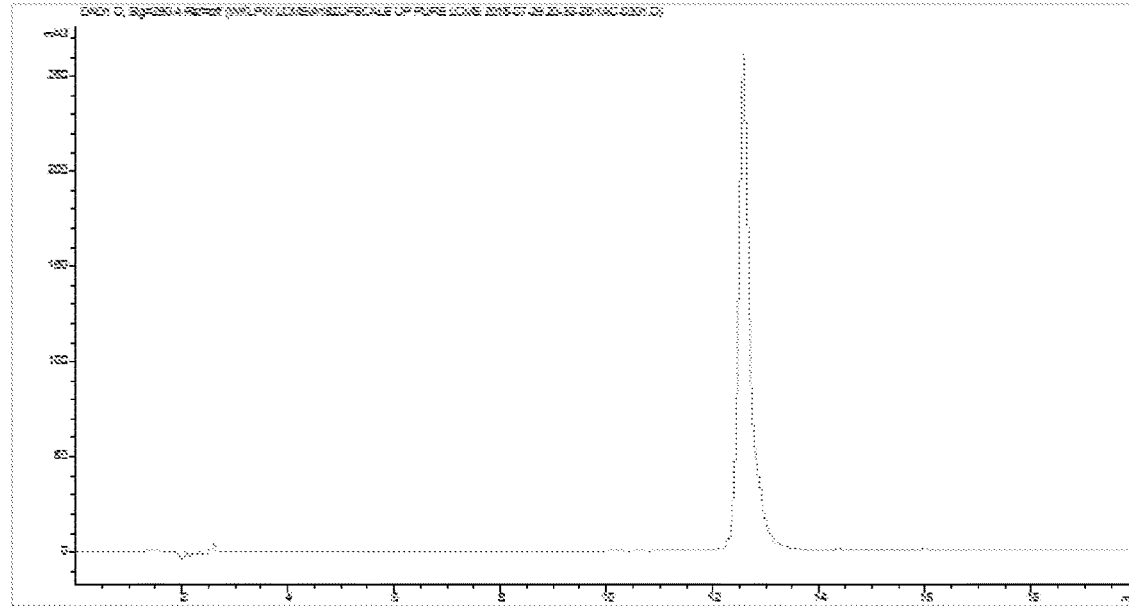
FIGS. 10A-10B. HPLC (a) and Mass (b) spectrum of A18.
Figure 10B:
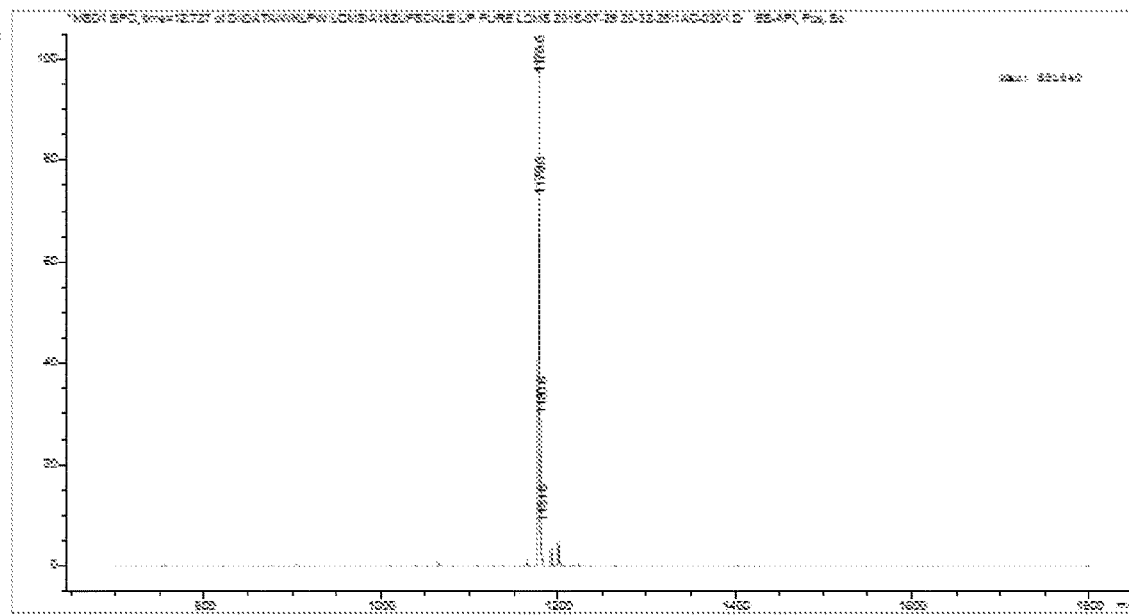
Figure 11A:
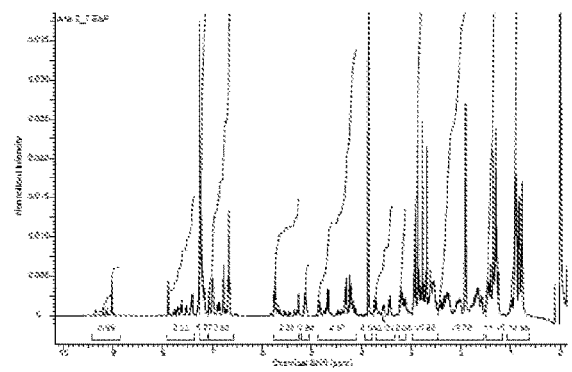
FIGS. 11A-11B. 1H-NMR (a) and 13C-NMR (b) of A18.
Figure 11B:
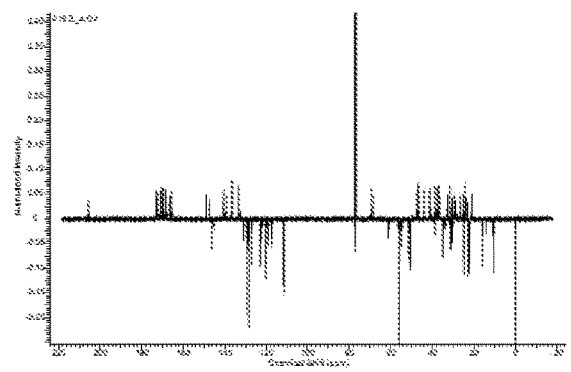
Figure 12A:
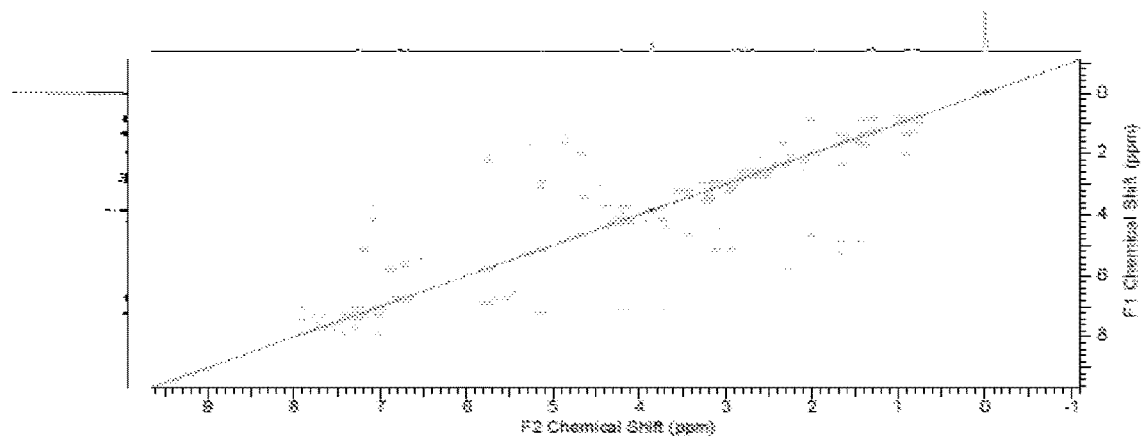
FIGS. 12A-12B. 2D COSY NMR (a) and 2D HSQC (b) of A18.
Figure 12B:
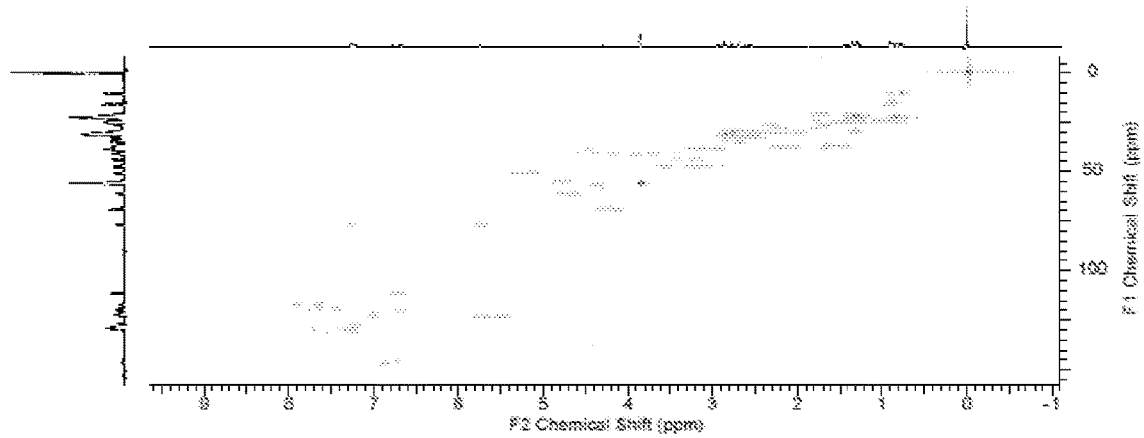

A 45,000 compound and 3000 pool rapafucin library were screened using the alamar blue cell viability assay with the human non-small cell lung cancer (NSCLC) cell line A549. At a final concentration of 400 nM per compound or 3 µM per pool of 15 rapafucins, we obtained over 50 hits that showed significant inhibition of A549 (FIG. 9). Ten of the most potent pools of hits were selected and each of the individual compounds from each pool was synthesized, followed by retesting of each rapafucin from those pools. Several potent rapafucin hits were discovered to inhibit cell proliferation of A549. In order to identify the most potent rapafucin hits, the initial set of active compounds was subjected for a follow-up dose-dependent analysis. Structures of the two most potent rapafucins A18 and E11 are shown in FIG. 1a. Each was resynthesized on preparative scale, purified by silica gel chromatography, followed by HPLC purification, and subjected to a series of detailed structure characterization (schemes I and II; FIGS. 10-14).

Dose-dependent inhibition of cell proliferation by A18 and E11 was next evaluated in several other human cancer cell lines, including breast cancer HCC1954, pancreatic cancer PANC10.05, leukemia Jurkat T and colon cancer RKO (FIGS. 1b and 1c). Two rapafucins were found to significantly inhibit the viability of those cancer cell lines with IC50 values ranging from 100 nM to 700 nM (Table 3). In addition, A18 shows more potent anti-proliferation activity than E11 in most cancer cell lines except pancreatic cancer PANC10.05. These results suggested that two rapafucins A18 and E11 have broad-spectrum of anticancer activity. (FIGS. 1 and 9; Table 3)

TABLE 3

Potency of A18 and E11 against the alamar blue assay on different cancer cell lines

|  | A549 | HCC1954 | PANC 10.05 | Jurkat T | HeLa | RKO | HEK293T |
|---|---|---|---|---|---|---|---|
| A18 IC50(nM) | 189.3 | 108.7 | 119.2 | 131.7 | 280.6 | 114.5 | 109.9 |
| E11 IC50(nM) | 367.4 | 159.4 | 79.77 | 250.9 | 383.3 | 714.2 | 154.4 |

To identify the molecular target of two rapafucins A18 and E11, a series of cell-based and biochemical studies were performed. Interestingly, it was found that the anti-proliferation effect of A18 and E11 can be slightly decreased when cells were cultured under high concentration of glucose (FIG. 16). Compared to low concentration of glucose (1 g/L), IC50 values of A18 and E11 increased 2-3 fold when cultured HEK293T or HeLa cells in high concentration of glucose (4 g/L). Since constant uptake of glucose is mediated by a family of transporters known as the facilitative glucose transporters (GLUTs) in mammalian cells, it was speculated that A18 and E11 might work through blocking the transport of glucose through GLUTs. Indeed, glucose uptake assay showed that A18 and E11 significantly inhibit glucose transport in A549 cells (FIG. 16). In addition, the inhibition of glucose transport induced by A18 and E11 occurred within 1 min after the assay started (FIG. 16a), suggesting that the inhibitory activity is likely to be via a direct and fast mechanism. Furthermore, this assay revealed that only 50% glucose uptake inhibition achieved for E11 when A549 cells were treated with drugs for 1 min. This suggested that the binding of E11 to its target is slower than A18 and two compounds might have a different working mechanism.

Figures 17A, 17B:
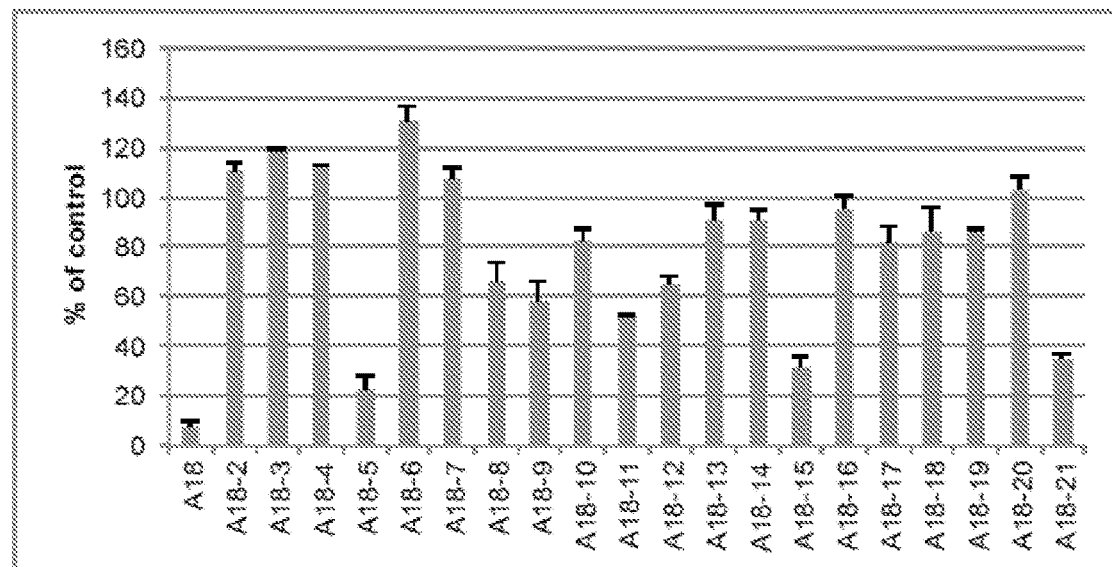
FIGS. 17A-17B. Inhibition of Glucose Transport by A18 and its analogues. (a) Inhibition of 2-deoxy-D-[$^3$H] glucose uptake in A549 cells by 100 nM of A18 and its analogues. (b) Amino acid sequences of A18 and its analogues.
Figure 18:
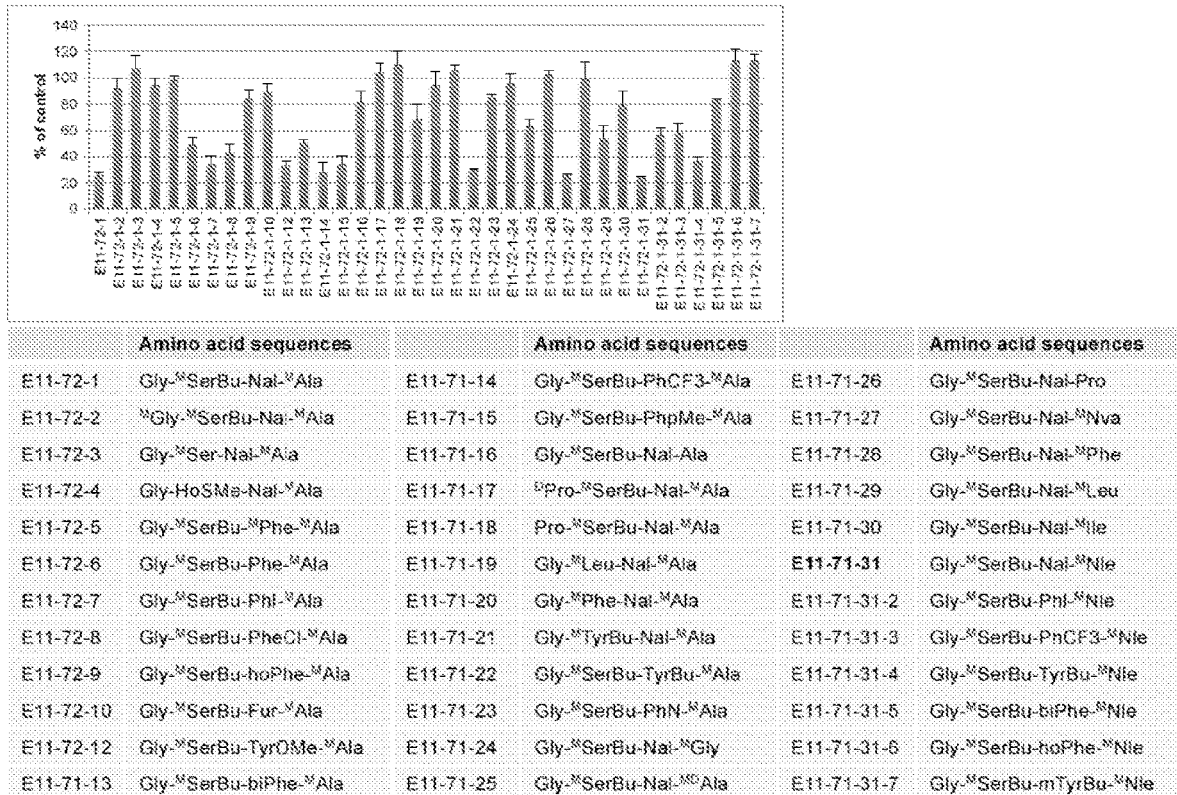
FIG. 18. Inhibition of Glucose Transport by E11 and its analogues. (a) Inhibition of 2-deoxy-D-[$^3$H] glucose uptake in A549 cells by 200 nM of E11 and its analogues. (b) Amino acid sequences of E11 and its analogues.

One or to two rounds of structure-activity (SAR) studies were then performed by synthesizing new analogs using different amino acid building blocks. Initial SAR analysis (FIGS. 17 and 18) revealed that replacement of any amino acids at the tetrapeptide moiety in A18 cannot be tolerated. However, replacement of the fourth amino acid N-methyl-L-Alanine with N-methyl-L-norvaline or N-methyl-L-norleucine in E11 could slightly increase in activity. E11-72-1-31 was named as E11 in the following context.

Figures 2A, 2B, 2C, 2D:
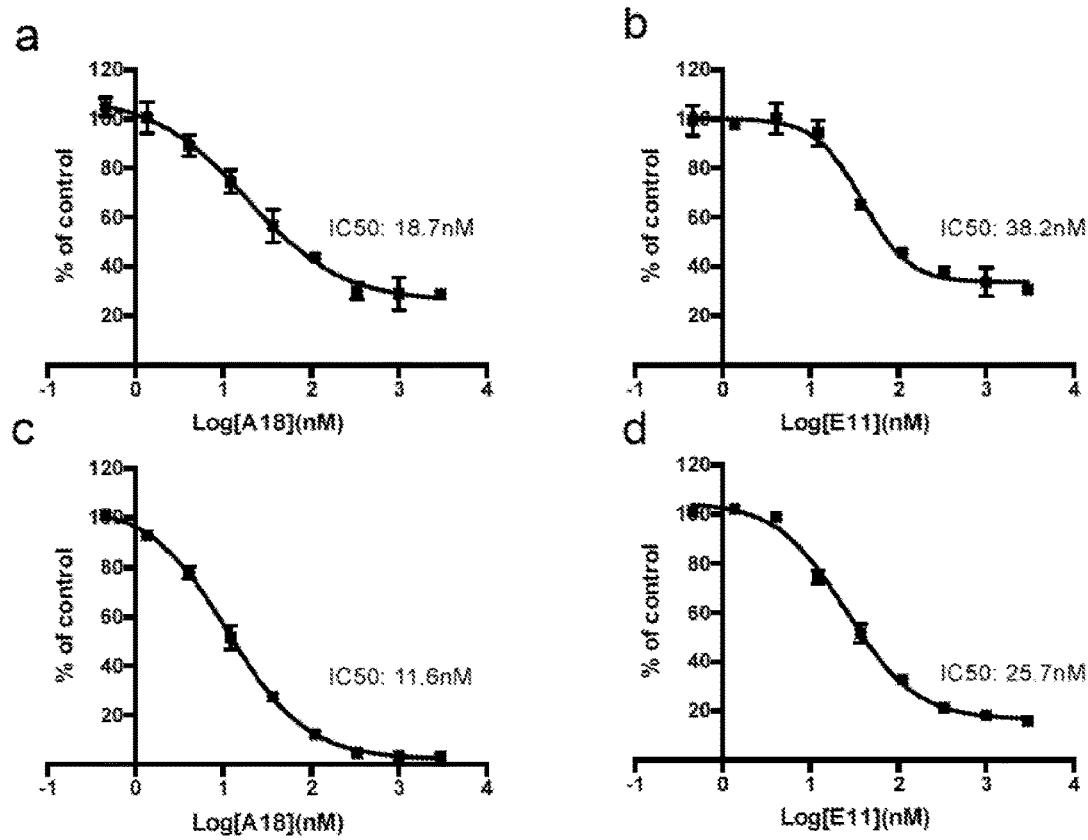
FIGS. 2A-2D. Inhibition of Glucose Transport by A18 and E11. (a) Inhibition of 3-O-methyl-D-[3H] glucose uptake in A549 cells by A18. (b) Inhibition of 3-O-methyl-D-[3H] glucose uptake in A549 cells by E11. (c) Inhibition of 2-deoxy-D-[3H] glucose uptake in A549 16 cells by A18. (d) Inhibition of 2-deoxy-D-[3H] glucose uptake in A549 cells by E11.

Direct action on glucose transporters was measured by monitoring uptake of 3H-labeled 3-O-methylglucose, which is transported by glucose transporters but not metabolized further, allowing the assessment of initial rate of glucose uptake. Under such conditions, A18 and E11 significantly inhibited uptake of this labeled glucose analog with IC50 values of 18.7 and 38.2 nM, respectively (FIGS. 2a and 2b). Initial uptake can also be assessed by measuring the uptake of 3H-labeled 2-deoxy-D-glucose, which gets into the cell through glucose transporters and is phosphorylated by hexokinase but cannot be metabolized further due to the lack of oxygen at the second position. A18 and E11 blocked the uptake of this labeled glucose analog with similar potency (FIGS. 2c and 2d). Compared to previously reported glucose transporter inhibitors, A18 and E11 are the first two compounds that have IC50 values below 50 nM (Table 1).

A18 and E11 were previously shown to have a broad spectrum of anticancer activity. If anticancer activity works through glucose transporter inhibition, it was speculated that the target of A18 and E11 is Glut1, as glut1 is responsible for basal glucose transport in almost all cell types and glut1 was upregulated in many cancer cells tested. To test this hypothesis, red blood cells (RBCs) were applied as a cell model because RBCs express Glut1 as their sole glucose transporter and have been frequently used in studying glucose transport. Indeed, the $^3$H-labeled 3-O-methylglucose uptake assays showed that A18 and E11 inhibited the glucose transport in RBCs with $IC_{50}$ values of 34.2 and 74.2 nM, respectively. To eliminate other possibilities, the glucose uptake assays were repeated in RBC-derived ghosts, in which all the intracellular proteins and enzymes were removed and only membrane-bound and membrane-associated proteins remained. Interestingly, the glucose uptake assays revealed that only A18 inhibited the glucose transport in RBCs—derived ghosts with an $IC_{50}$ of 49.5 nM. However, E11 totally lost its inhibitory activity, suggesting that E11 might work through binding to other intracellular protein first and then blocking glucose transport. (see FIGS. 2, 3 and 15-18)

Figures 19A, 19B, 19C:
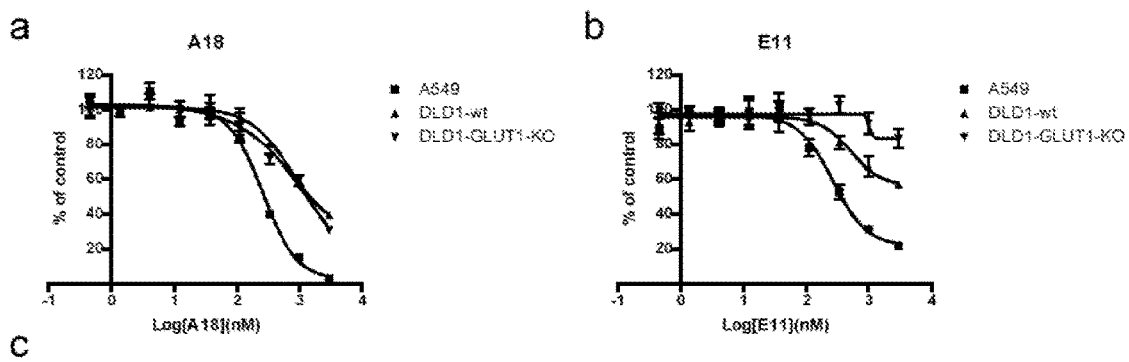
FIGS. 19A-19C. E11 is a specific inhibitor of Glut1. (a)(b) Inhibition of cell proliferation in A549, DLD-1 wild type and Glut1 knock out cells by A18 and E11. (c) Potency of A18 and E11 against the alamar blue assay in A549, DLD-1 wild type and Glut1 knock out cells.
Figures 20A, 20B, 20C:
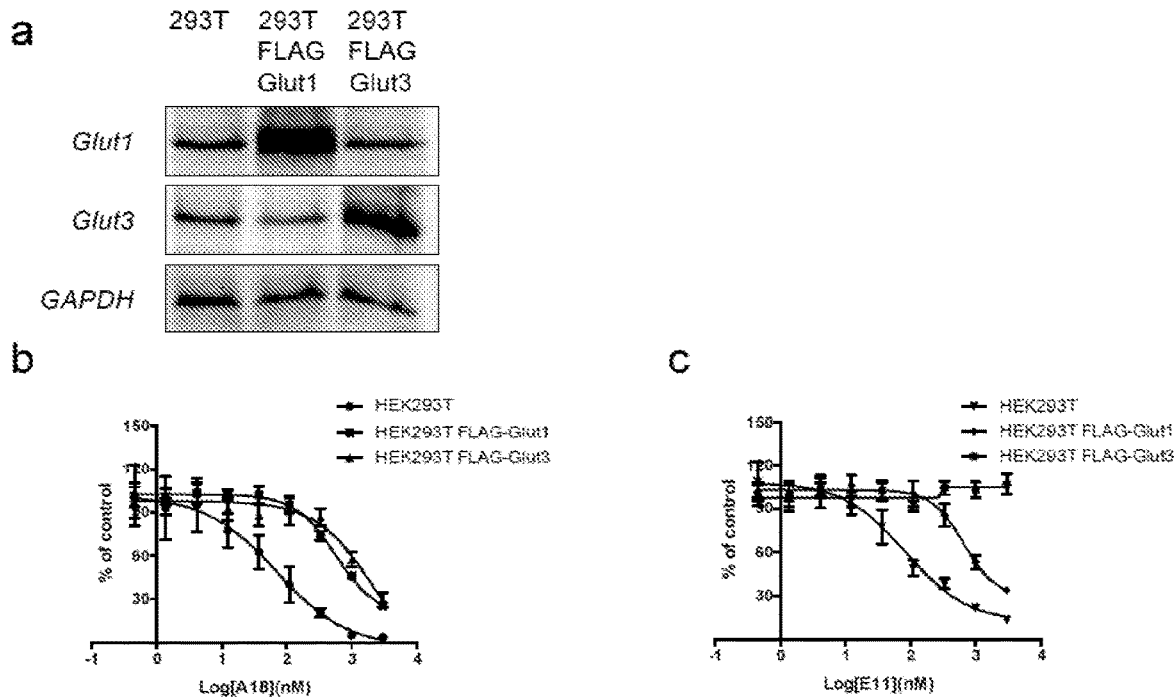
FIGS. 20A-20C. E11 is a specific inhibitor of Glut1. (a) Glut1 and Glut3 protein levels of wild type, Glut1 and Glut3 overexpression cells analyzed by western blotting. (b)(c) Inhibition of cell proliferation in HEK293T, Glut1 and Glut3 overexpression cells by A18 and E11.

Up to now, at least 14 different isoforms of GLUTs have been identified in human cells. It was then asked whether A18 and E11 are specific inhibitors of GLUT1. To answer this question, colon cancer DLD-1 wild type and GLUT1 gene knock out cell lines were chosen as a cell model (FIG. 4a). Interestingly, $^3$H-labeled 2-deoxy-D-glucose uptake and alamar blue cell viability assays showed that A18 still strongly inhibited the glucose transport and cell proliferation in both cell lines. However, E11 didn't show any inhibition in DLD-1 GLUT1 gene knock out cells but kept inhibitory activity in wild type cells (FIGS. 4b and 19). This suggested that E11, but not A18, is a specific inhibitor of GLUT1. GLUTs that are most relevant to cancer are Glut1 and Glut3. To obtain additional evidence, Glut1 and Glut3 in HEK 293T cells were overexpressed and an alamar blue cell viability assay was performed again. As expected, E11 indeed didn't show any inhibition in GLUT3 overexpression cells but kept partial inhibitory activity in GLUT1 overexpression cells (FIG. 20 and Table 4), strongly supporting the hypothesis that E11 is a specific inhibitor of GLUT1. (see FIGS. 4, 19, 20, 26; Table 4).

TABLE 4

Potency of A18 and E11 against the alamar blue assay in HEK 293T and its Glut1 or Glut3 overexpression cells

|  | HEK 293T | HEK 293T FLAG-Glut1 | HEK 293T FLAG-Glut3 |
|---|---|---|---|
| A18 IC50 (nM) | 69.0 | 573.2 | 2353 |
| E11 IC50 (nM) | 84.8 | 658.5 | No activity |

Figures 5A, 5B, 5C:
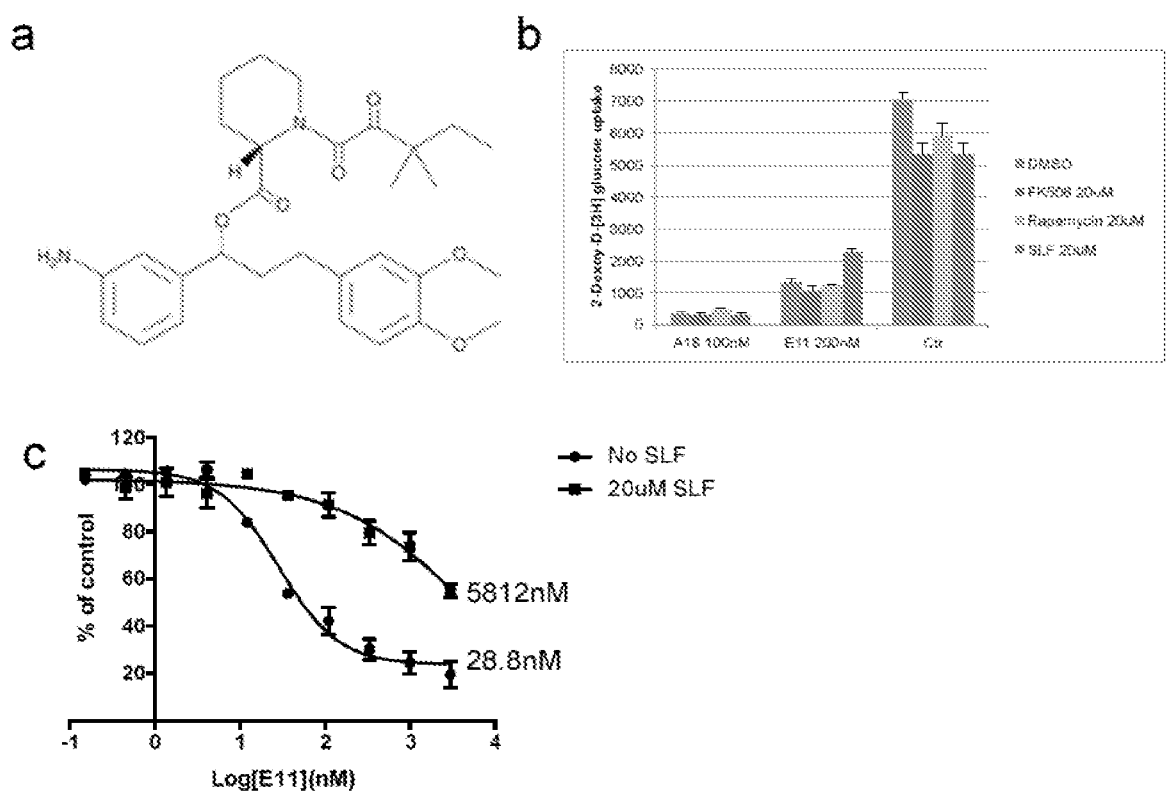
FIGS. 5A-5C. E11 shows FKBP-dependent. (a) Chemical structure of SLF. (b)(c) Inhibition of 2-deoxy-D-[3H] glucose uptake in A549 cells by E11, A18 and FKBP ligands.

Given the underlying principle of the design of the rapafucin libraries, it was next explored whether the inhibition of GLUT1 by A18 or E11 is dependent on FKBP. A hallmark of FKBP dependence is that the cellular effects would be antagonized by another unrelated FKBP binding ligands with no or orthogonal biological activity as has been shown for FK506 and rapamycin. For unknown reasons, both FK506 and rapamycin were unable to antagonize inhibitory effects of A18 or E11 on 3H-labeled 2-deoxy-D-glucose uptake (FIG. 5b). However, synthetic ligand of FKBP (SLF)(FIG. 5a) significantly impaired the inhibitory activity of E11 (FIG. 5c), suggesting that the activity of E11 requires FKBP.

Figure 6A:
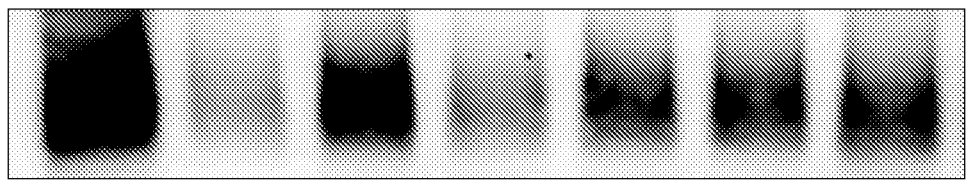
FIGS. 6A-6B. Identification of direct interaction of A18 and E11 to Glut1. Glut1 protein levels of A18 (a) or E11 (b) pull down samples analyzed by western blotting.
Figure 6B:
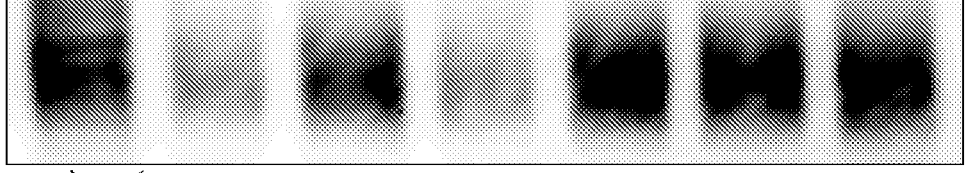
Figure 21:
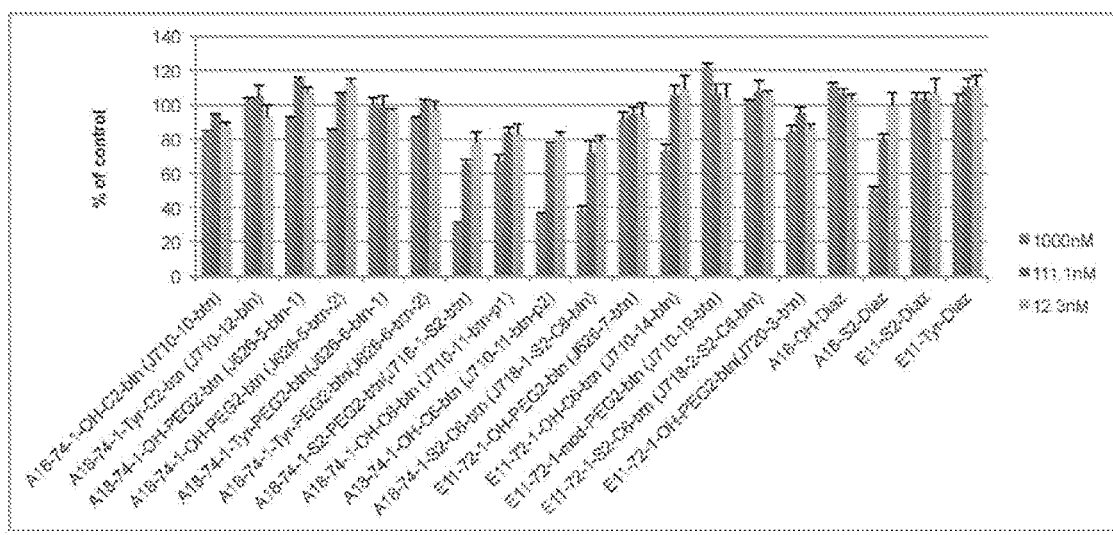
FIG. 21. Inhibition of 2-deoxy-D-[$^3$H] glucose uptake in A549 cells by A18, E11 and their affinity probes.
Figure 22A:
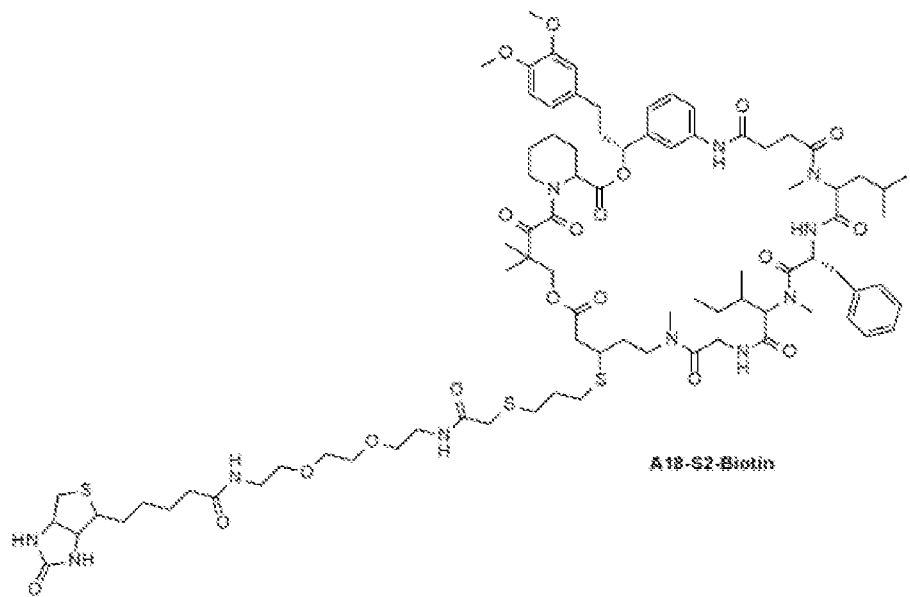
FIGS. 22A-22B. Chemical structures of A18-S2-Biotin (a) and E11-OH Biotin (b). A18 and E11 can pull down Glut1.
Figure 22B:
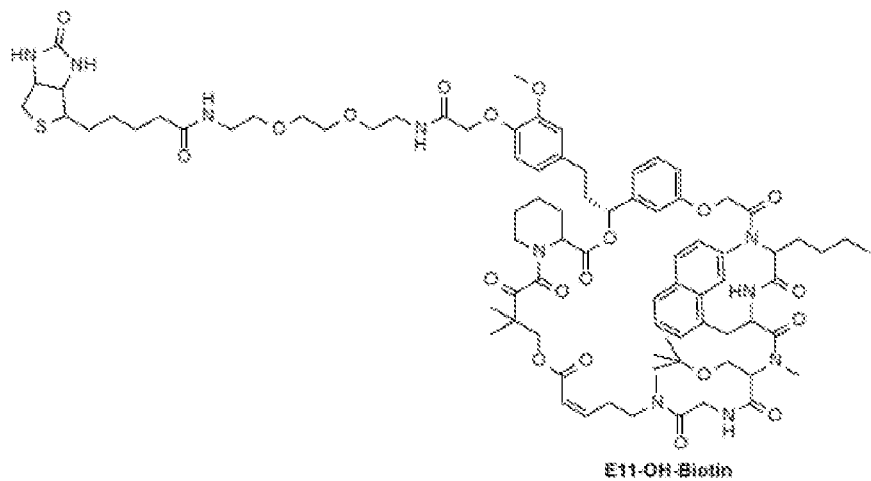

After showing that GLUT1 was very likely to be the target of A18 and E11, the direct interaction of A18 and E11 to GLUT1 was then examined. A series of biotin or diazrine-alkyne rapafucin conjugates through different positions were synthesized. Glucose uptake assays showed that only a few of conjugates kept inhibitory activity in A549 cells (FIG. 21). Using the most potent biotin-rapafucin conjugates (FIG. 22), pulldown assays followed by Western blot using anti-GLUT1 antibodies were performed. It was found that the biotin-rapafucin conjugates are able to pull down GLUT1 from RBC-derived ghosts cell lysate (FIG. 6). Importantly, the binding of the biotin-rapafucin probe to GLUT1 is competed by rapafucin. Moreover, the binding of the A18 probe to GLUT1 cannot be competed by E11 and vice versa, suggesting that two rapfucins might have a different binding position. Finally, as expected, the binding of the rapafucin probe to GLUT1 cannot be competed by FK506 and Rapamycin. Taken together, pulldown assays showed that rapafucin A18 and E11 can bind directly to GLUT1. (FIGS. 6, 21, 22 and 27)

Figure 23:
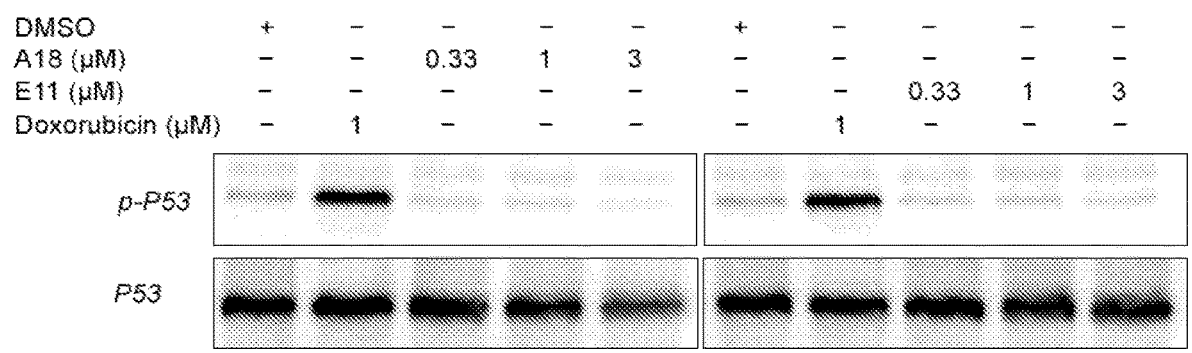
FIG. 23. A18 and E11 do not induce DNA damage in HEK 293T cells within 72 h. HEK 293 Ts were treated with increasing concentration of A18 or E11, a negative control (DMSO), and a positive control (doxorubicin) for 72 h and cell lysates were subjected to SDS-PAGE followed by Western blot analysis with the indicated antibodies.
Figure 24:
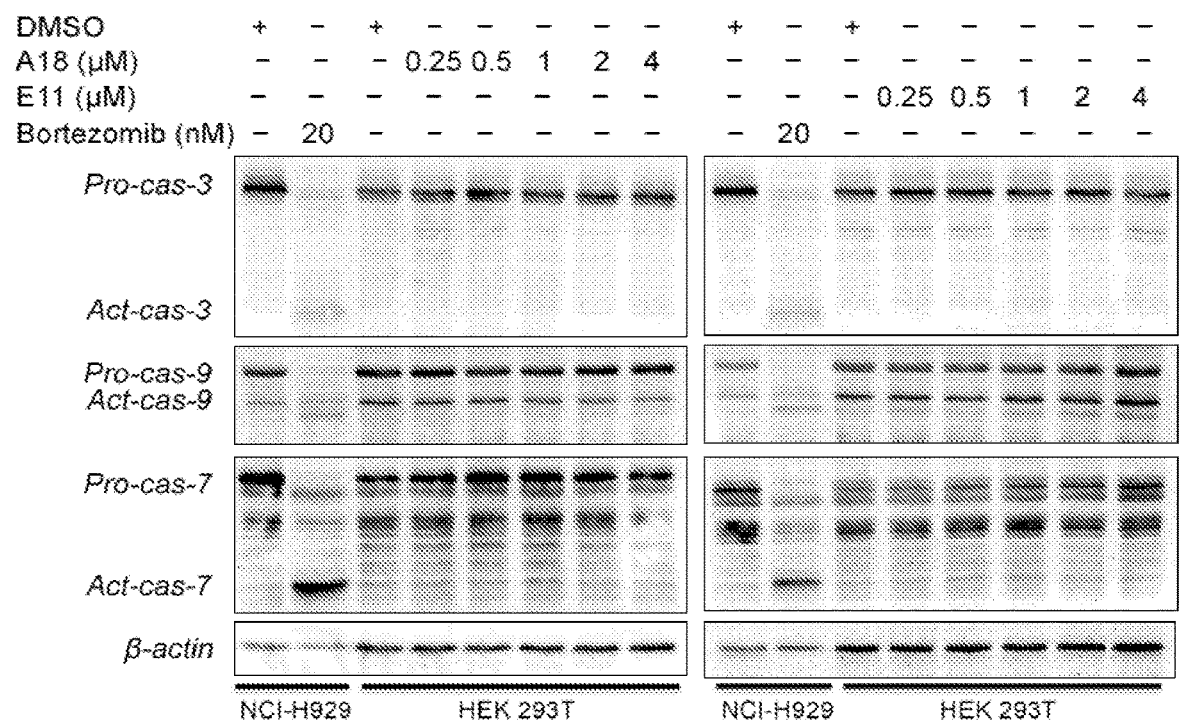
FIG. 24. A18 and E11 do not induce apoptosis in HEK 293T cells within 24 h. HEK 293 Ts were treated with A18 or E11 for the different concentration and cell lysates were subjected to SDS-PAGE followed by Western blot analysis with the indicated antibodies.
Figure 27:
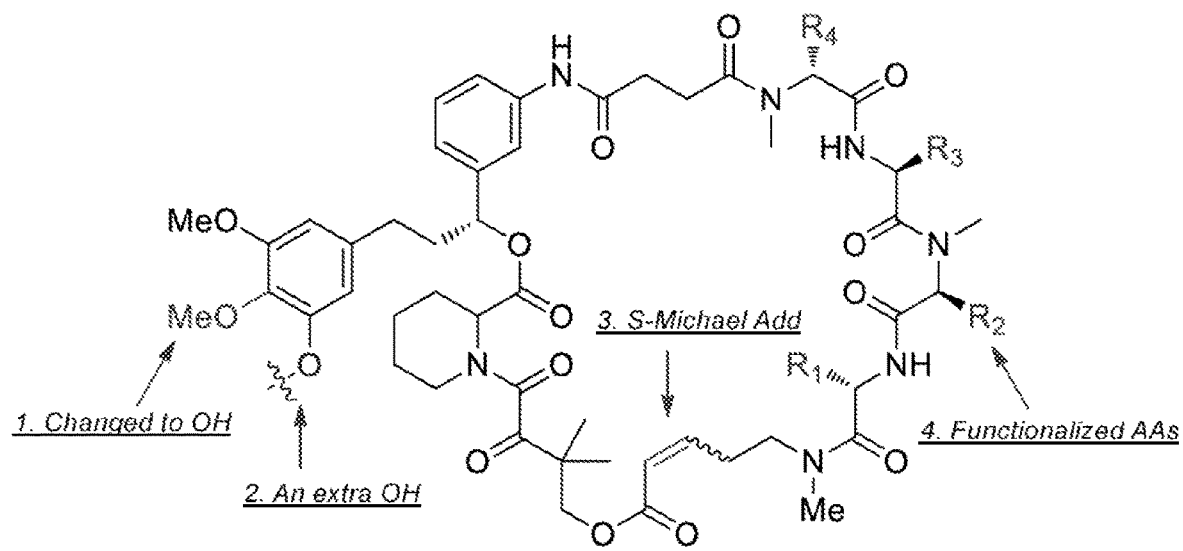
FIG. 27. Bottom-up approach.

Whether A18 and E11 killed cancer cells through cell death or a different pathway was investigated. There was no increase in phosphor-p53 level and active caspase 3, 7 and 9 in HEK 293T cells, suggesting that A18 and E11 do not induce DNA damage or apoptosis (FIGS. 23 and 24). However, flow cytometric analysis revealed that A18 and E11 treatment led to cell cycle arrest. A18 and E11 treatment resulted in approximately 10% more cells in S phase. This finding for the first time demonstrated that glucose transporter inhibitor treatment led to S phase cell cycle arrest.

Figure 7A:
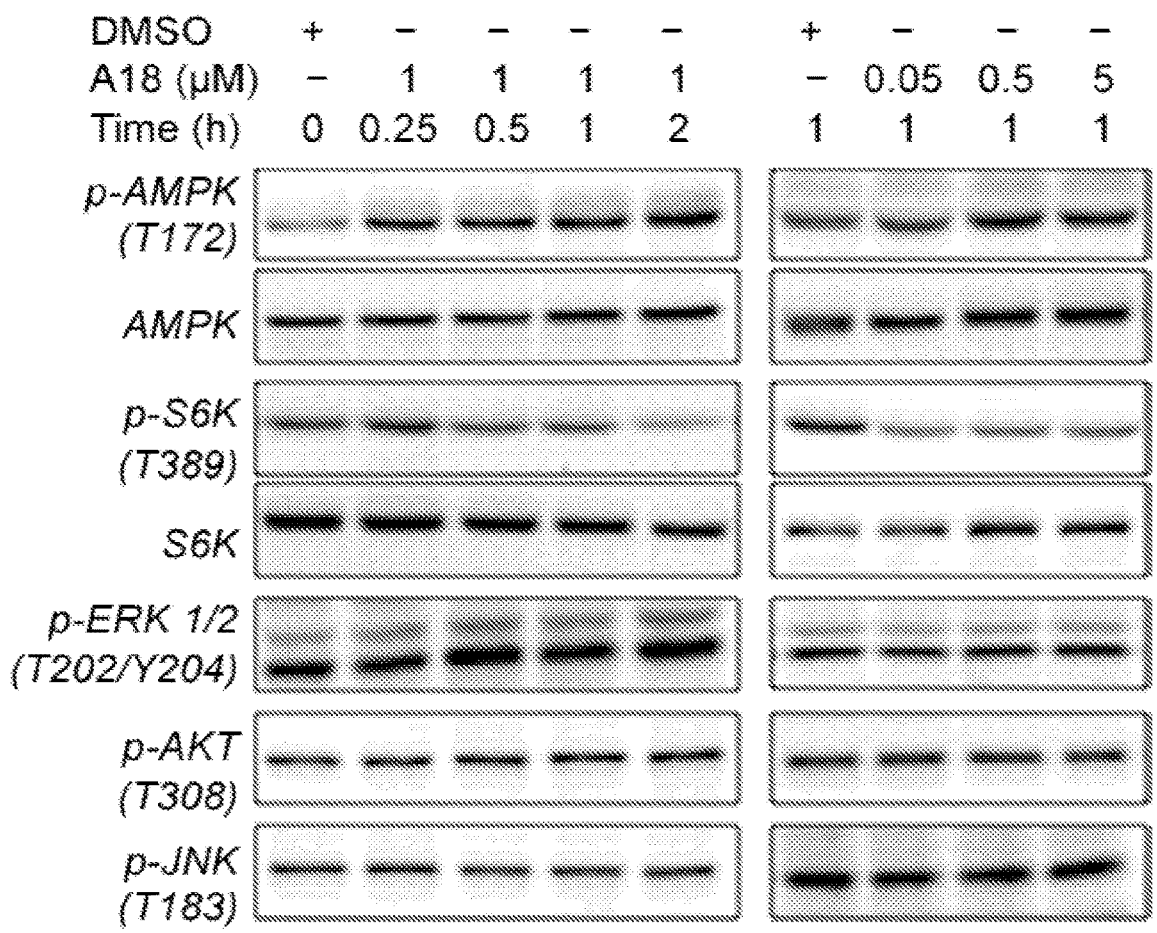
FIGS. 7A-7B. (a) A18 activates AMPK and inhibits S6K in HEK 293T cells. HEK 293 Ts were treated with A18 for the different time (left) or different concentration (right), and cell lysates were subjected to SDS-PAGE followed by Western blot analysis with the indicated antibodies. (b) A18 and E11 activate AMPK and inhibit S6K in HEK 293T cells.
Figure 7B:
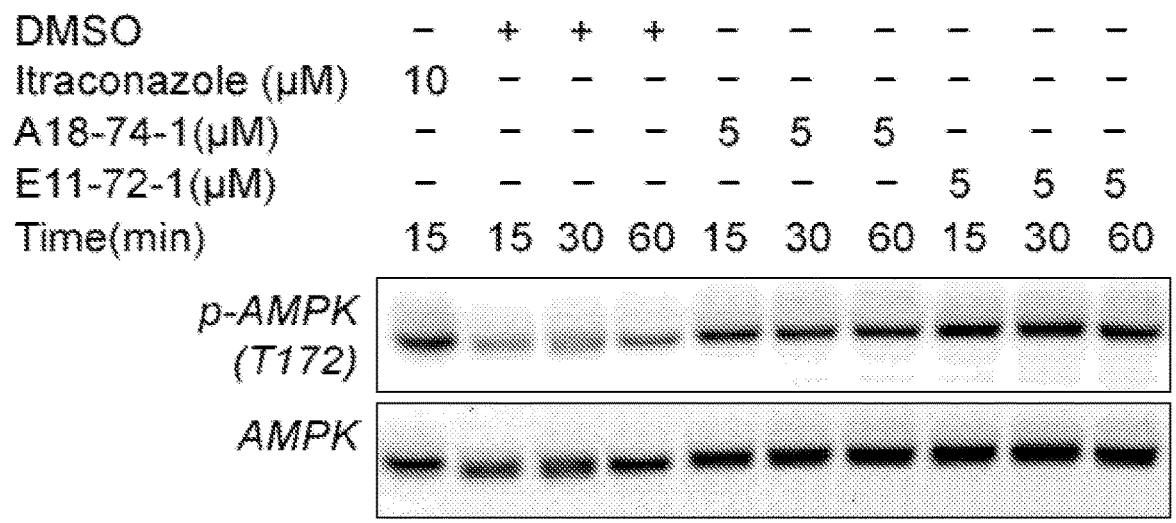
Figure 8:
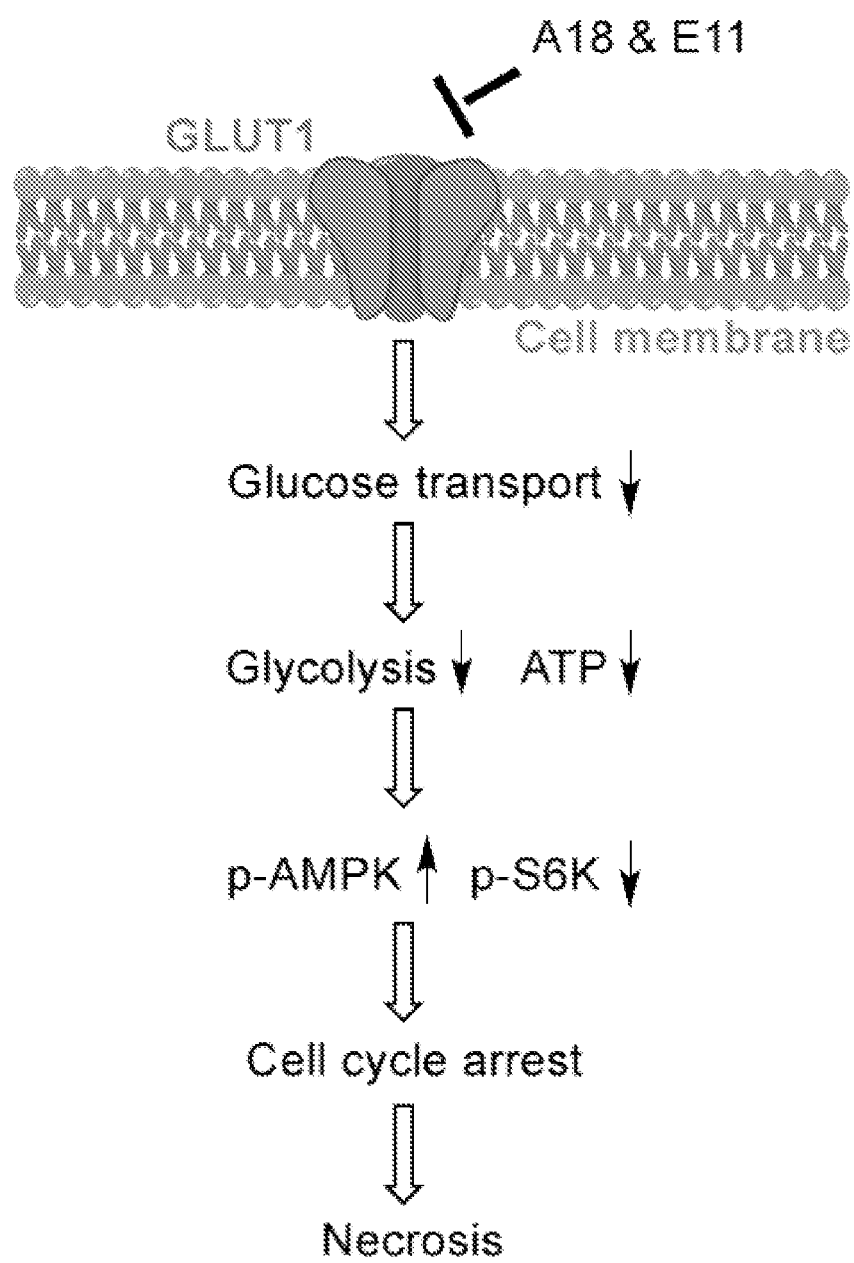
FIG. 8. A proposed mechanism for the anticancer activity of A18 and E11.

Whether A18 and E11 treatment affect key cell growth signaling proteins was examined next. Western blot analysis revealed that A18 and E11 are capable of inducing phosphorylation of AMPK and causing mTOR inhibition. But it has no effects on the phosphorylation of ERK, AKT or JNK (FIG. 7). As previously reported, AMPK is likely to act as the key link between the ATP reduction and the subsequent cancer cell inhibition. (FIGS. 7 and 23-25). Based on the data reported here, the working model for A18 and E11 was proposed as outlined in FIG. 8. After A18 or E11 treatment, glucose supply in cancer cells dramatically decreased, followed by some key glycolytic enzymes and metabolites (ATP) decreased. These led to upregulation of phosphorylation of AMPK and downregulation of phosphorylation of S6K. All these changes induced cell cycle arrest, necrosis or senescence, and finally induced cancer cell inhibition. (FIG. 8)

Figures 28A, 28B, 28C, 28D:
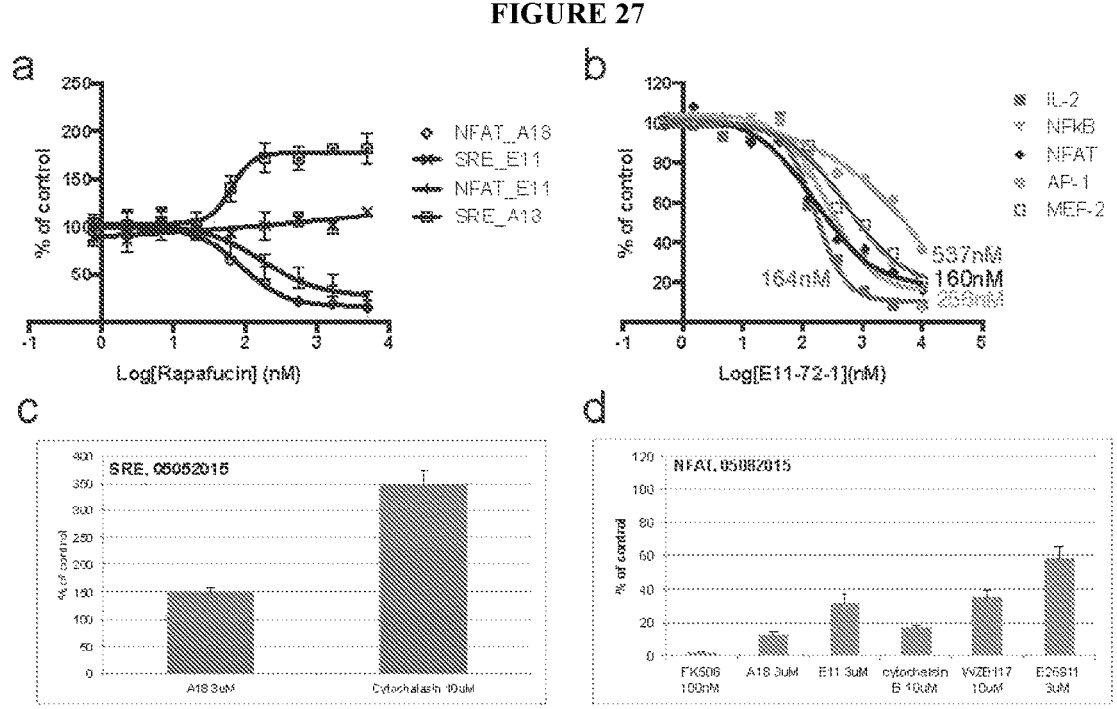
FIGS. 28A-28D. (a) A18 and E11 inhibit NFAT and A18, but not E11, stimulates SRE reporter gene signal. (b) E11 inhibits NFAT, NF-κB and IL2, but not MEF-2 or AP-1 pathways, in Jurkat T cells. (c) Glucose inhibitor stimulates SRE reporter gene signal. (d) Glucose inhibitors inhibit NFAT reporter gene signal.

Both A18 and E11 have shown immunosuppressive activity, blocking NFAT reporter gene activation and IL-2 production (see e.g., FIG. 28). As such, they can be used as immunosuppressive agents that have applications in treating organ transplantation rejection and all kinds of autoimmune diseases. Examples of immune related diseases that can be treated include but are not limited to: Acute disseminated encephalomyelitis (ADEM), Addison's disease, Ankylosing spondylitis, Antiphospholipid antibody syndrome, Autoimmune hemolytic anemia, Autoimmune hepatitis, Autoimmune inner ear disease, Autoimmune Lymphoproliferative Syndrome (ALPS), Autoimmune polyendocrine/polyglandular syndrome, Autoimmune thrombocytoipenia purpura, Balo disease, Behçet disease, Bullous pemphigoid, Cardiomyopathy, Celiac sprue-dermatitis herpetiformis, Chronic fatigue immune dysfunction syndrome (CFIDS), Chronic inflammatory demyelinating neuropathy, Cicatrical pemphigoid, Coeliac disease, Cold agglutinin disease, CREST syndrome, Crohn's disease, Cystic fibrosis, Degos disease, Dermatomyositis, Diabetes (Type I or Juvenile onset), Early onset dementia, Eczema, Endotoxin shock, Essential mixed cryoglobulinemia, Familial Mediterranean fever, Fibromyalgia, Fibromyositis, Goodpasture's syndrome, Graves' disease, Guillain-Barré syndrome (GBS), Hashimoto's thyroidosis, Hidradenitis suppurativa, Idiopathic pulmonary fibrosis, Idiopathic thrombocytopenic purpura, IgA nephropathy, Lambert-Eaton Myasthenic Syndrome, Leukemia, Lichen planus, Ménière disease, Mixed connective tissue disease, Multiple sclerosis, Multiphasic disseminated encephalomyelitis, Myasthenia gravis, Neuromyelitis Optica, Paraneoplastic Syndromes, Pemphigus, Pemphigus vulgaris, Pernicious anaemia, Polyarteritis nodosum, Polychondritis, Polymyalgia rhematica, Polymyositis, Primary agammaglobulinemia, Primary biliary cirrhosis, Plaque Psoriasis, Psoriatic arthritis, Raynaud phenomenon, Reiter syndrome, Restenosis following angioplasty, Rheumatic fever, Rheumatoid arthritis, Rheumatoid psoriasis, Sarcoidosis, Scleroderma, Sepsis, Sezary's disease, Sjögren's syndrome, Stiff-person syndrome, Lupus including Systemic lupus erythematosis (SLE), Takayasu arteritis, Temporal arteritis (also known as "giant cell arteritis"), Transplant or Allograft rejection, Ulcerative colitis, Uveitis, Vasculitis, Vitiligo, Graft vs Host disease, pustular psoriasis, and Wegener's granulomatosis (now termed Granulomatosis with Polyangiitis (GPA), inflammatory bowel disease, Acute necrotizing hemorrhagic leukoencephalitis, Agammaglobulinemia, Alopecia areata, Amyloidosis, Anti-GBM/Anti-TBM nephritis, Antiphospholipid syndrome (APS), Autoimmune angioedema, Autoimmune aplastic anemia, Autoimmune dysautonomia, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thyroid disease, Autoimmune urticarial, Axonal & neuronal neuropathies, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Cogans syndrome, Congenital heart block, Coxsackie myocarditis, CREST disease, Demyelinating neuropathies, Dermatitis herpetiformis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibrosing alveolitis, Giant cell arteritis (temporal arteritis), Giant cell myocarditis, Glomerulonephritis, Granulomatosis with Polyangiitis (GPA) (formerly called Wegener's Granulomatosis), Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen sclerosus, Ligneous conjunctivitis, Linear IgA disease (LAD), Lupus (SLE), Lyme disease, chronic, Microscopic polyangiitis, Mooren's ulcer, Mucha-Habermann disease, Myositis, Narcolepsy, Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, POEMS syndrome, Type I, II, & III autoimmune polyglandular syndromes, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Reactive Arthritis, Reflex sympathetic dystrophy, Relapsing polychondritis, Restless legs syndrome, Retroperitoneal fibrosis, Rheumatic fever, Schmidt syndrome, Scleritis, Sperm & testicular autoimmunity, Subacute bacterial endocarditis (SBE), Susac's syndrome, Sympathetic ophthalmia, Thrombocytopenic purpura (TTP), Tolosa-Hunt syndrome, Transverse myelitis, Type 1 diabetes, Undifferentiated connective tissue disease (UCTD) and Vesiculobullous dermatosis.

Although the invention has been described with reference to the above example, it will be understood that modifications and variations are encompassed within the spirit and scope of the invention. Accordingly, the invention is limited only by the following claims.

What is claimed is:
1. A compound with the following structure:

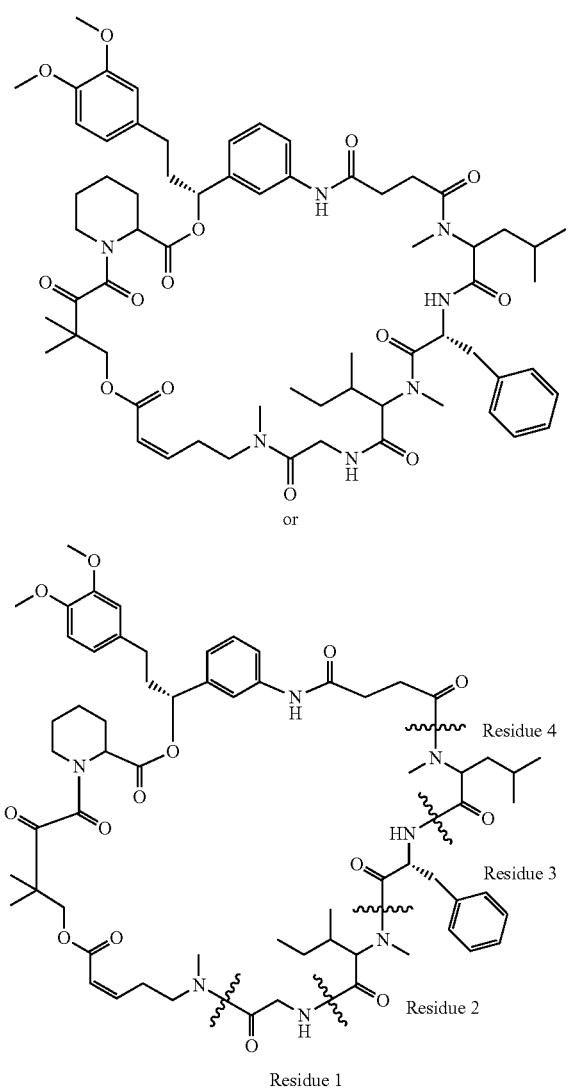

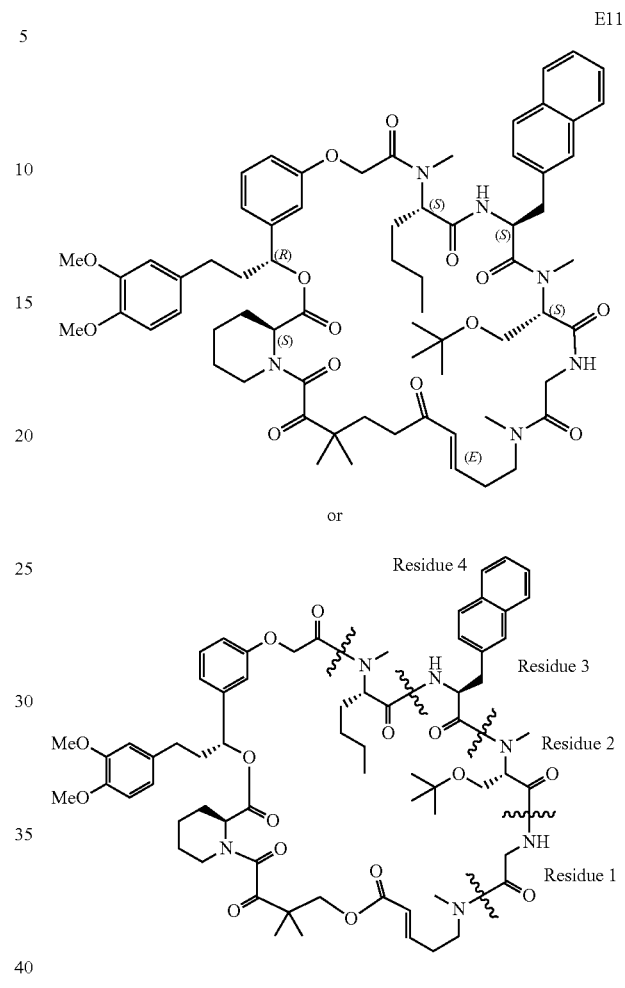

wherein residue 1, residue 2, residue 3, and residue 4 are exchanged and selected from below:

| Compound No. | Peptide (residue 1-residue 2-residue 3-residue 4) |
|---|---|
| A18-2 | mGly-mIle-dPhe-mLeu |
| A18-3 | Pro-mIle-dPhe-mLeu |
| A18-4 | dPro-mIle-dPhe-mLeu |
| A18-5 | Gly-mVal-dPhe-mLeu |
| A18-8 | Gly-mNle-dPhe-mLeu |
| A18-9 | Gly-mNva-dPhe-mLeu |
| A18-10 | Gly-mLeu-dPhe-mLeu |
| A18-15 | Gly-mIle-mdPhe-mLeu |
| A18-16 | Gly-mIle-dLeu-mLeu |
| A18-17 | Gly-mIle-dPhe-Leu |
| A18-18 | Gly-mIle-dPhe-mIle |
| A18-19 | Gly-mIle-dPhe-mNva |
| A18-20 | Gly-mIle-dPhe-mNle |
| A18-21 | Gly-mIle-dPhe-mVal |
| A18-22 | Gly-mIle-dPhe-mPhe; | or wherein residue 1, residue 2, residue 3, and residue 4 are exchanged and selected from below:

| Compound No. | Peptide (residue 1-residue 2-residue 3-residue 4) |
|---|---|
| E11-72-1 | Gly-mSerBu-Nal-mAla |
| E11-72-2 | mGly-mSerBu-Nal-mAla |
| E11-72-3 | Gly-mSer-Nal-mAla |
| E11-72-4 | Gly-HoSerMe-Nal-mAla |
| E11-72-5 | Gly-mSerBu-mPhe-mAla |
| E11-72-6 | Gly-mSerBu-Phe-mAla |
| E11-71-16 | Gly-mSerBu-Nal-Ala |
| E11-71-17 | dPro-mSerBu-Nal-mAla |
| E11-71-18 | Pro-mSerBu-Nal-mAla |
| E11-71-19 | Gly-mLeu-Nal-mAla |
| E11-71-20 | Gly-mPhe-Nal-mAla |
| E11-71-24 | Gly-mSerBu-Nal-mGly |
| E11-71-25 | Gly-mSerBu-Nal-mdAla |
| E11-71-26 | Gly-mSerBu-Nal-Pro |
| E11-71-27 | Gly-mSerBu-Nal-mNva |
| E11-71-28 | Gly-mSerBu-Nal-mPhe |
| E11-71-29 | Gly-mSerBu-Nal-mLeu |
| E11-71-30 | Gly-mSerBu-Nal-mIle |
| E11-71-31 | Gly-mSerBu-Nal-mNle. |

2. A compound with the following structure:

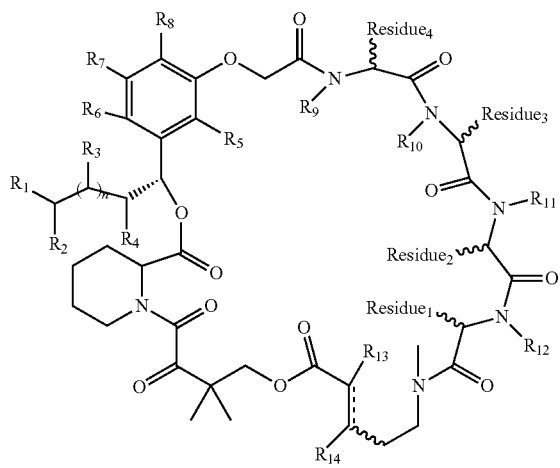

wherein
n is an integer selected from 0 to 6;
$R_1$ is selected from the group consisting of

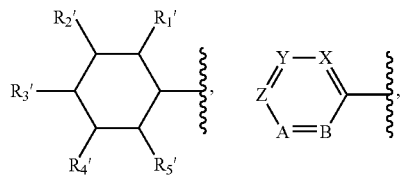 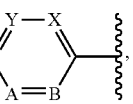

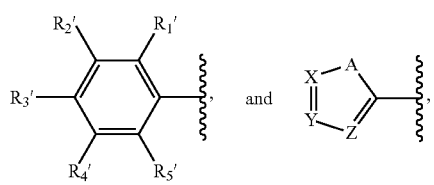 and 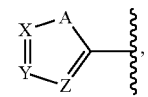, when $R_1$ is

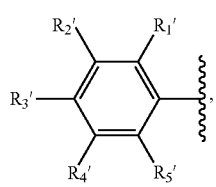

$R_1'$, $R_2'$, $R_3'$, $R_4'$, and $R_5'$ are independently selected from the group consisting of OH, $NH_2$, SH, CN, H, OAc, and OMe, when $R_1$ is

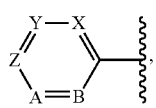

A, B, X, Y, and Z are independently C or N, when $R_1$ is

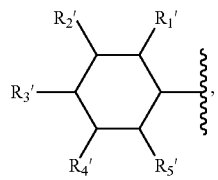

$R_1'$, $R_2'$, $R_3'$, $R_4'$, and $R_5'$ are independently selected from the group consisting of OH, $NH_2$, SH, H, OAc, and OMe, when $R_1$ is

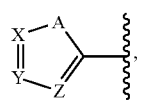

A, X, Y, and Z are independently selected from the group consisting of —(CH)m-, O, N, and S, where m is an integer selected from 1 to 2;

$R_2$, $R_3$, and $R_4$ are independently selected from the group consisting of H, methyl, ethyl, propyl, isopropyl, phenyl, OH, $NH_2$, SH, and CN;

$R_5$, $R_6$, $R_7$, and $R_8$ are independently selected from the group consisting of methyl, ethyl, propyl, isopropyl, phenyl, OH, $NH_2$, SH, and CN;

$R_9$, $R_{10}$, $R_{11}$, and $R_{12}$ are independently selected from the group consisting of hydrogen and methyl;

$R_{13}$ and $R_{14}$ are independently selected from the group consisting of OH, $NH_2$, SH, CN, and hydrogen;

"$\equiv$" represents a double bond with E or Z configuration; and the amino acids with residues 1 to 4 are selected from the group consisting of

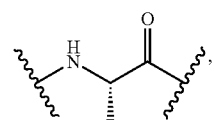

Ala

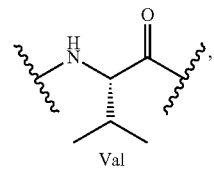 [SMILES: *N[C@H](C(*)=O)C(C)C]

Val

33
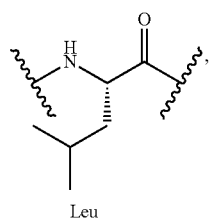 [SMILES: *N[C@@H](CC(C)C)C(*)=O]
Leu
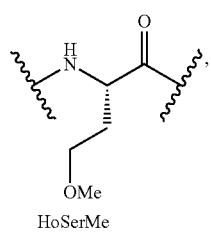 [SMILES: *N[C@@H](CCOC)C(*)=O ; "HoSerMe"]
HoSerMe
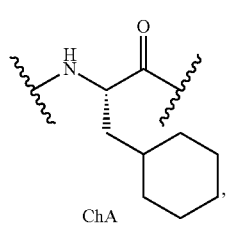 [SMILES: *N[C@@H](CC1CCCCC1)C(*)=O]
ChA
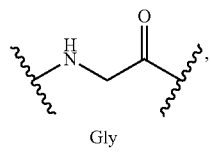 [SMILES: *NCC(*)=O]
Gly
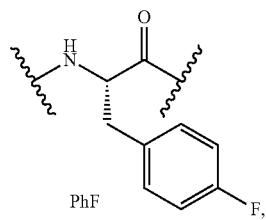
PhF
34
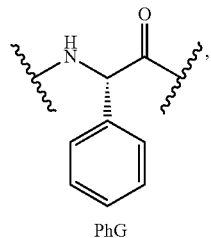 [SMILES: *N[C@H](C(*)=O)c1ccccc1]
PhG
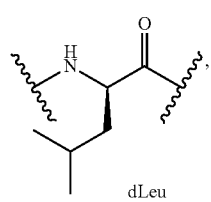 [SMILES: *N[C@H](CC(C)C)C(*)=O]
dLeu
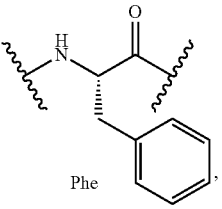 [SMILES: *N[C@@H](Cc1ccccc1)C(*)=O]
Phe
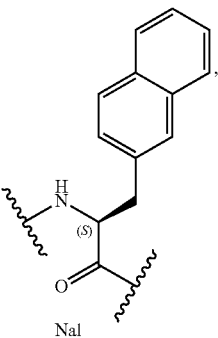
Nal
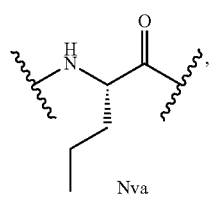 [SMILES: *N[C@@H](CCC)C(*)=O]
Nva

| 35 | 36 |
|---|---|
| 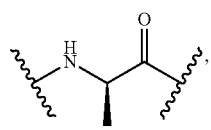
dAla | 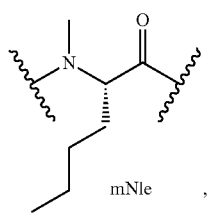
mNle, |
| 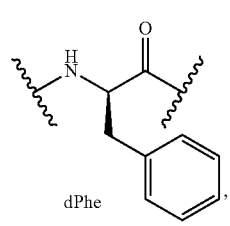 [SMILES: *N[C@H](Cc1ccccc1)C(*)=O]
dPhe, | 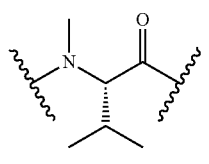
mVal, |
| 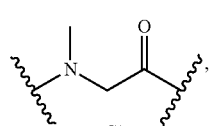
mGly, | 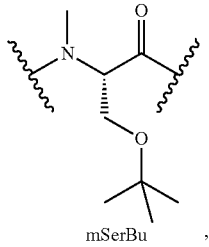
mPhe, |
| 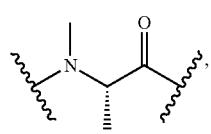
mAla, | 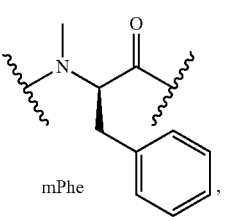
mSerBu, |
| 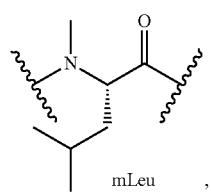 [SMILES: *C(=O)[C@H](CC(C)C)N(*)C]
mLeu, | 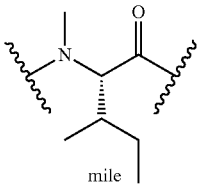
mPhe, and |
| 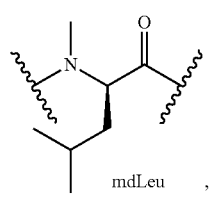 [SMILES: *C(=O)[C@@H](CC(C)C)N(*)C]
mdLeu, | 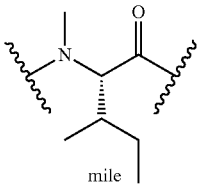
mIle, | or residue 1, 2, 3, or 4 together with the adjacent nitrogen form
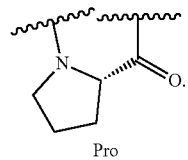
Pro
3. A compound according to claim 1, wherein the compound is Formula A18.
4. A compound according to claim 1, wherein the compound is Formula E11.
* * * * *